(12) United States Patent
Renner et al.

(10) Patent No.: US 7,381,801 B2
(45) Date of Patent: Jun. 3, 2008

(54) CHIMERIZED GM-CSF ANTIBODIES

(75) Inventors: Christoph Renner, Homburg (DE); Antony Burgess, Melbourne (AU); Andrew Scott, Melbourne (AU)

(73) Assignee: Ludwig Institute for Cancer Research, New York, NY (US)

( * ) Notice: Subject to any disclaimer, the term of this patent is extended or adjusted under 35 U.S.C. 154(b) by 255 days.

(21) Appl. No.: 10/365,123

(22) Filed: Feb. 12, 2003

(65) Prior Publication Data

US 2004/0053365 A1    Mar. 18, 2004

Related U.S. Application Data

(60) Provisional application No. 60/355,838, filed on Feb. 13, 2002.

(51) Int. Cl.
*C07K 16/24* (2006.01)

(52) U.S. Cl. ............................. 530/388.23; 530/387.3

(58) Field of Classification Search ............. 530/387.1
See application file for complete search history.

(56) References Cited

U.S. PATENT DOCUMENTS 5,919,452 A * 7/1999 Le et al. .................. 424/133.1

OTHER PUBLICATIONS

American Type Cell Culture (ATCC) Cell lines and Hybridomas, Hay et al., eds., 8th edition, Rockville, Maryland, 1994, p. 193.*
Human Granulocyte-Macrophage Colony-Stimulating . . . Antibody, Nice, et al., *Growth Factor*, 3:159-169 (1990)—pp. 159-169.
Monoclonal Antibodies . . . In Vitro, Dempsey, et al.—*Hybridoma*, vol. 9. No. 6, (1990) pp. 545-558.

* cited by examiner

*Primary Examiner*—Michail Belyavskyi
*Assistant Examiner*—Zachary Skelding
(74) *Attorney, Agent, or Firm*—Fulbright & Jaworski LLP

(57) ABSTRACT

Chimeric antibodies, as well as fusion proteins which comprise chimeric antibodies, are disclosed. The antibodies bind to GM-CSF, CD-30, and G250 antigen. The fusion proteins include biologically active portions of tumor necrosis factor, or full length tumor necrosis factor. Expression vectors adapted for production of the antibodies, as well as methods for manufacturing these, are also disclosed.

3 Claims, 6 Drawing Sheets

US 7,381,801 B2

CHIMERIZED GM-CSF ANTIBODIES

RELATED APPLICATION

This application claims priority of application Ser. No. 60/355,838, filed Feb. 13, 2002, and incorporated by reference in its entirety.

FIELD OF THE INVENTION

This invention relates to the field of molecular immunology, generally, and to vectors useful for expression of proteins, especially antibodies, such as fully human, humanized, and chimeric antibodies, as well as fusion proteins which incorporate the antibody and a protein or protein fragment, in eukaryotic cells, mammalian cells in particular. The resulting antibodies and fusion proteins are also a feature of the invention.

BACKGROUND AND PRIOR ART

One serious problem with using murine antibodies for therapeutic applications in humans is that they quickly raise a human anti-mouse response (HAMA) which reduces the efficacy of the antibody in patients, and prevents continued administration thereof. Parallel issues arise with the administration of antibodies from other, non-human species. One approach to overcoming this problem is to generate so-called "chimeric" antibodies. These can comprise murine variable regions, and human constant regions (Boulianne et al. (1984) *Nature* 312(5995): 643-646.; incorporated by reference herein in its entirety). Although chimeric antibodies contain murine sequences and can elicit an anti-mouse response in humans (LoBuglio et al. (1989) *Proc. Natl. Acad. Sci. USA* 86(11): 4220-4224; incorporated by reference herein in its entirety), trials with chimeric antibodies in the area of hematological disease (e.g., Non-Hodgkin-Lymphoma; Witzig et al. (1999) *J. Clin. Oncol.* 17(12): 3793-3803.; incorporated by reference herein in its entirety) or autoimmune disease (e.g., rheumatoid arthritis, chronic inflammatory bowel disease; Van den Bosch; et al, Lancet 356(9244):1821-2 (2000), incorporated by reference herein in its entirety) have led to FDA approval and demonstrate that these molecules have significant clinical potential and efficacy.

Recent studies have indicated that granulocyte-macrophage colony stimulating growth factor (GM-CSF) plays a role in the development of rheumatoid arthritis (RA) (Cook, et al., Arthritis Res. 2001, 3:293-298, incorporated by reference herein in its entirety) and possibly other inflammatory diseases and conditions. Therefore, it would be of interest to develop a drug which would block GM-CSF and its effect on cells. The present invention provides a chimeric antibody, targeting the GM-CSF molecule, which has blocking capacity.

The increased use of chimeric antibodies in therapeutic applications has created the need for expression vectors that effectively and efficiently produce high yields of functional chimeric antibodies in eukaryotic cells, such as mammalian cells, which are preferred for production. The present invention provides novel expression vectors, transformed host cells and methods for producing chimeric antibodies in mammalian cells, as well as the antibodies themselves and fusion proteins containing them.

BRIEF DESCRIPTION OF THE FIGURES

FIG. 5 shows results of an assay testing the effect of increasing concentration of murine or chimeric 19/2 mAbs, on TF-1 cells grown in the presence of a constant amount of human GM-CSF.

SUMMARY OF INVENTION

Figure 1:
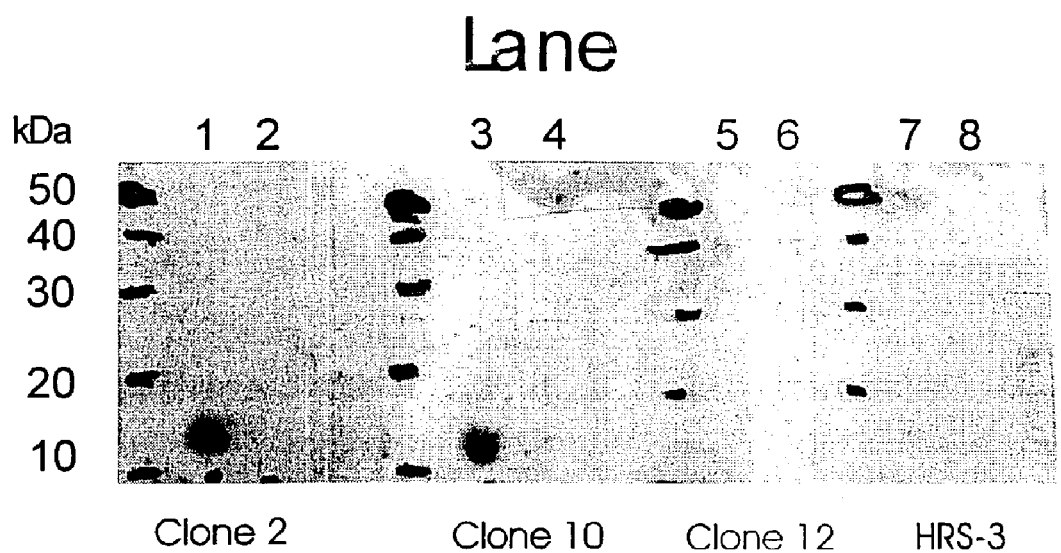
FIG. 1 shows the binding of recombinant, chimeric anti GM-CSF antibody via Western Blotting.

The present invention provides expression vectors which are useful in the expression of proteins, such as antibodies, especially fully human, humanized or chimerized antibodies, and fusion proteins containing these. Both light chains and heavy chains can be expressed. The expression vectors of the present invention comprise a human elongation factor 1 α (EF1α) promoter/enhancer sequence, an internal ribosome entry site (IRES) sequence (U.S. Pat. No. 4,937,190; incorporated herein in its entirety), a nucleotide sequence that confers neomycin resistance to a cell containing the expression vector, and a nucleotide sequence under control of a simian virus 40 promoter (SV40) that confers ampicillin resistance to a cell containing the expression vector. In a preferred embodiment, the EF1α promoter/enhancer sequence is upstream and adjacent to a nucleotide sequence encoding a chimeric light chain.

The expression vector of the present invention may contain a nucleotide sequence encoding any immunoglobulin light chain. In a preferred embodiment the light chain variable region is of murine origin, and the light chain constant region is either human kappa or human lambda. In a more preferred embodiment, the chimeric light chain variable region is derived from a murine antibody that binds to GM-CSF, CD-30, or G250 and in especially preferred embodiments, to the human forms of these molecules.

The present invention also provides a further expression vector useful in the expression of proteins, such as antibodies, especially fully human, humanized or chimeric antibodies, and fusion proteins containing these. This second embodiment differs from the first in that instead of the neomycin resistance sequence, described supra, it comprises a nucleotide sequence which encodes dihydrofolate reductase or "dhfr," which generates resistance against the well known selection marker methotrexate. Such an expression vector may contain nucleotide sequences encoding any antibody or portion thereof, such as heavy or light chains of fully human, humanized or chimerized antibodies. In a preferred embodiment, a heavy chain is expressed, where the variable region is of murine origin, and the heavy chain constant region is human IgG1. In a more preferred embodiment, the chimeric heavy chain variable region is derived from a murine antibody that binds CD-30, GM-CSF or G250, preferably the human forms of these.

In another embodiment, the present invention provides host cells transformed or transfected with any one of the expression vectors of the present invention. In a preferred embodiment, a host cell, preferably a eukaryotic cell, more preferably a mammalian cell, is transformed or transfected with an expression vector comprising a chimeric immunoglobulin light chain and an expression vector comprising a chimeric immunoglobulin heavy chain. The present invention contemplates prokaryotic and eukaryotic cells, such as mammalian cells, insect cells, bacterial or fungal cells. In a preferred embodiment, the host cell is a human or Chinese Hamster Ovary ("CHO") cell.

The present invention also provides methods for the recombinant production of a chimeric immunoglobulin light or heavy chain comprising the step of culturing a transformed or transfected host cell of the present invention. In one embodiment, the methods of the present invention further comprise the isolation of the chimeric immunoglobulin light or heavy chain.

The present invention also provides methods for the recombinant production of a fully human, humanized or chimeric immunoglobulin comprising culturing a host cell that has been transformed or transfected with an expression vector comprising a chimeric immunoglobulin light chain and an expression vector comprising a chimeric immunoglobulin heavy chain, or an expression vector encodes both chains. In one embodiment, the methods of the present invention further comprise the self-assembly of the chimeric heavy and light chain immunoglobulins and isolation of the chimeric immunoglobulin. Methods for accomplishing this are well known in the art.

The present invention also provides the chimeric immunoglobulin light chain, heavy chain or assembled chimeric immunoglobulin produced by the methods of the present invention. In another embodiment, the present invention provides compositions comprising the chimeric immunoglobulin light chain, heavy chain or assembled chimeric immunoglobulin of the present invention and a pharmaceutically acceptable carrier.

DETAILED DESCRIPTION OF INVENTION

1. Definitions

As used herein "chimerized" refers to an immunoglobulin such as an antibody, wherein the heavy and light chains of the variable regions are not of human origin and wherein the constant regions of the heavy and light chains are of human origin.

"Humanized" refers to an immunoglobulin such as an antibody, wherein the amino acids directly involved in antigen binding, the so-called complementary determining regions (CDR), of the heavy and light chains are not of human origin, while the rest of the immunoglobulin molecule, the so-called framework regions of the variable heavy and light chains, and the constant regions of the heavy and light chains are of human origin.

"Fully human" refers to an immunoglobulin, such as an antibody, where the whole molecule is of human origin or consists of an amino acid sequence identical to a human form of the antibody.

"Immunoglobulin" or "antibody" refers to any member of a group of glycoproteins occurring in higher mammals that are major components of the immune system. As used herein, "immunoglobulins" and "antibodies" comprise four polypeptide chains—two identical light chains and two identical heavy chains that are linked together by disulfide bonds. An immunoglobulin molecule includes antigen binding domains, which each include the light chains and the end-terminal portion of the heavy chain, and the $F_c$ region, which is necessary for a variety of functions, such as complement fixation. There are five classes of immunoglobulins wherein the primary structure of the heavy chain, in the $F_c$ region, determines the immunoglobulin class. Specifically, the alpha, delta, epsilon, gamma, and mu chains correspond to IgA, IgD, IgE, IgG and IgM, respectively. As used herein "immunoglobulin" or "antibody" includes all subclasses of alpha, delta, epsilon, gamma, and mu and also refers to any natural (e.g., IgA and IgM) or synthetic multimers of the four-chain immunoglobulin structure.

"Antigen-binding fragment", "antigen-binding domain" and "Fab fragment" all refer to the about 45 kDa fragment obtained by papain digestion of an immunoglobulin molecule and consists of one intact light chain linked by a disulfide bond to the N-terminal portion of the contiguous heavy chain. As used herein, "$F(ab)_2$ fragment" refers to the about 90 kDa protein produced by pepsin hydrolysis of an immunoglobulin molecule. It consists of the N-terminal pepsin cleavage product and contains both antigen binding fragments of a divalent immunoglobulin, such as IgD, IgE, and IgG. Neither the "antigen-binding fragment" nor "$F(ab)_2$ fragment" contain the about 50 kDa $F_c$ fragment produced by papain digestion of an immunoglobulin molecule that contains the C-terminal halves of the immunoglobulin heavy chains, which are linked by two disulfide bonds, and contain sites necessary for compliment fixation.

"Epitope" refers to an immunological determinant of an antigen that serves as an antibody-binding site. Epitopes can be structural or conformational.

"Hybridoma" refers to the product of a cell-fusion between a cultured neoplastic lymphocyte and a normal, primed B- or T-lymphocyte, which expresses the specific immune potential of the parent cell.

"Heavy chain" refers to the longer & heavier of the two types of polypeptide chain in immunoglobulin molecules that contain the antigenic determinants that differentiate the various Ig classes, e.g., IgA, IgD, IgE, IgG, IgM, and the domains necessary for complement fixation, placental transfer, mucosal secretion, and interaction with $F_c$ receptors.

"Light chain" refers to the shorter & lighter of the two types of polypeptide chain in an Ig molecule of any class. Light chains, like heavy chains, comprise variable and constant regions.

"Heavy chain variable region" refers to the amino-terminal domain of the heavy chain that is involved in antigen binding and combines with the light chain variable region to form the antigen-binding domain of the immunoglobulin.

"Heavy chain constant region" refers to one of the three heavy chain domains that are carboxy-terminal portions of the heavy chain.

"Light chain variable region" refers to the amino-terminal domain of the light chain and is involved in antigen binding and combines with the heavy chain to form the antigen-binding region.

"Light chain constant region" refers to the one constant domain of each light chain. The light chain constant region consists of either kappa or lambda chains.

"Murine anti-human-GM-CSF 19/2 antibody" refers to a murine monoclonal antibody that is specific for human GM-CSF. This antibody is well known and it has been studied in detail. See Dempsey, et al, Hybridoma 9:545-58 (1990); Nice, et al, Growth Factors 3:159-169 (1990), both incorporated by reference.

"Effective amount" refers to an amount necessary to produce a desired effect.

"Antibody" refers to any glycoprotein of the immunoglobulin family that non-covalently, specifically, and reversibly binds a corresponding antigen.

"Monoclonal antibody" refers to an immunoglobulin produced by a single clone of antibody-producing cells. Unlike polyclonal antiserum, monoclonal antibodies are monospecific (e.g., specific for a single epitope of a single antigen).

"Granulocytes" include neutrophils, eosinophils, and basophils.

"GM-CSF" refers to a family of glycoprotein growth factors that control the production, differentiation, and function of granulocytes and monocytes-macrophages. Exemplary, but by no means the only form of such molecules, can be seen in U.S. Pat. No. 5,602,007, incorporated by reference.

"Inflammatory condition" refers to immune reactions that are either specific or non-specific. For example, a specific reaction is an immune reaction to an antigen. Examples of specific reactions include antibody responses to antigens, such as viruses and allergens, including delayed-type hypersensitivity, including psoriasis, asthma, delayed type hypersensitivity, inflammatory bowel disease, multiple sclerosis, viral pneumonia, bacterial pneumonia, and the like. A non-specific reaction is an inflammatory response that is mediated by leukocytes such as macrophages, eosinophils and neutrophils. Examples of non-specific reactions include the immediate swelling after a bee sting, and the collection of polymorphonuclear (PMN) leukocytes at sites of bacterial infection. Other "inflammatory conditions" within the scope of this invention include, e.g., autoimmune disorders such as psoriasis, rheumatoid arthritis, lupus, post-ischemic leukocyte mediated tissue damage (reperfusion injury), frost-bite injury or shock, acute leukocyte-mediated lung injury (acute respiratory distress syndrome or ARDS), asthma, traumatic shock, septic shock, nephritis, acute and chronic inflammation, and platelet-mediated pathologies such as ateriosclerosis and inappropriate blood clotting.

"Pharmaceutically acceptable carrier" refers to any carrier, solvent, diluent, vehicle, excipient, adjuvant, additive, preservative, and the like, including any combination thereof, that is routinely used in the art.

Physiological saline solution, for example, is a preferred carrier, but other pharmaceutically acceptable carriers are also contemplated by the present invention. The primary solvent in such a carrier may be either aqueous or non-aqueous. The carrier may contain other pharmaceutically acceptable excipients for modifying or maintaining pH, osmolarity, viscosity, clarity, color, sterility, stability, rate of dissolution, and/or odor. Similarly, the carrier may contain still other pharmaceutically acceptable excipients for modifying or maintaining the stability, rate of dissolution, release, or absorption or penetration across the blood-brain barrier.

The fully human, humanized or chimerized antibodies of the present invention may be administered orally, topically, parenterally, rectally or by inhalation spray in dosage unit formulations that contain conventional non-toxic pharmaceutically acceptable carriers, adjuvants and vehicles. As used herein, "parenterally" refers to subcutaneous, intravenous, intramuscular, intrasternal, intrathecal, and intracerebral injection, including infusion techniques.

The fully human, humanized or chimerized antibodies may be administered parenterally in a sterile medium. The antibodies, depending on the vehicle and concentration used, may be suspended or dissolved in the vehicle. Advantageously, adjuvants such as local anesthetics, preservatives and buffering agents can be dissolved in the vehicle. The most preferred routes of administration of the pharmaceutical compositions of the invention are subcutaneous, intramuscular, intrathecal or intracerebral administration. Other embodiments of the present invention encompass administration of the composition in combination with one or more agents that are usually and customarily used to formulate dosages for parenteral administration in either unit dose or multi-dose form, or for direct infusion.

Active ingredient may be combined with the carrier materials in amounts necessary to produce single dosage forms. The amount of the active ingredient will vary, depending upon the type of antibody used, the host treated, the particular mode of administration, and the condition from which the subject suffers. Preferably, the amount of fully human, humanized or chimerized anti-GM-CSF immunoglobulin, for example, is a therapeutically effective amount which is sufficient to decrease an inflammatory response or ameliorate the symptoms of an inflammatory condition. It will be understood by those skilled in the art, however, that specific dosage levels for specific patients will depend upon a variety of factors, including the activity of the specific immunoglobulins utilized, the age, body weight, general health, sex, diet, time of administration, route of administration, and rate of excretion, drug combination and the severity of the particular disease undergoing therapy. Administration of the fully human, humanized or chimerized immunoglobulins of the present invention may require either one or multiple dosings.

Regardless of the manner of administration, however, the specific dose is calculated according to approximate body weight or body surface area of the patient. Further refinement of the dosing calculations necessary to optimize dosing for each of the contemplated formulations is routinely conducted by those of ordinary skill in the art without undue experimentation, especially in view of the dosage information and assays disclosed herein.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Cloning Strategy for 19/2 Heavy (H) and Light (L) Variable (V)-region Genes

Total RNA from the hybridoma producing murine 19/2 antibody was obtained by standard RNA isolation techniques (Chomczynski et al. (1987) *Anal. Biochem.* 162: 156-159.; incorporated by reference herein in its entirety). First strand cDNA was prepared using a commercially available, first strand cDNA synthesis kit and priming with d(T)18 for both the heavy and light chains (Renner et al. (1998) *Biotechniques* 24(5): 720-722.; incorporated by reference herein in its entirety). The resulting cDNA was subjected to PCR using combinations of primers for the heavy and light chains. The nucleotide sequences of the 5' primers for the heavy and light chains are shown in Tables 1 and 2 respectively. The 3' primers are shown in Table 3. The light chain primer hybridized within the mouse kappa constant region not far from the V-C junction. The heavy chain 3' primer hybridised within the CH-1 constant region of mouse heavy chain subgroup 1 not far from the V-CH1 junction.

TABLE 1

Oligonucleotide primers for the 5' region of Mouse Heavy Variable (MHV) domains.

| | | SEQ ID NO:1 |
|---|---|---|
| MHV-1: | 5'ATGAAATGCAGCTGGGTCATSTTCTTC 3' | 1 |
| MHV-2: | 5'ATGGGATGGAGCTRATCATSYTCTT 3' | 2 |
| MHV-3: | 5'ATGAAGWTGTGGTTAAACTGGGTTTTT 3' | 3 |
| MHV-4: | 5'ATGRACTTTGWYTCAGCTTGRTTT 3' | 4 |
| MHV-5: | 5'ATGGACTCCAGGCTCAAMAGTTTTCCTT 3' | 5 |
| MHV-6: | 5'ATGGCTGTCYTRGSGCTRCTCTTCTGC 3' | 6 |
| MHV-7: | 5'ATGGRATGGAGCKGGRTCTTTMTCTT 3' | 7 |
| MHV-8: | 5'ATGAGAGTGCTGATTCTTTTGTG 3' | 8 |
| MHV-9: | 5'ATGGMTTGGGTGTGGAMCTTGCTATTCCTG 3' | 9 |
| MHV-10: | 5'ATGGGCAGACTTACATTCTCATTCCTG 3' | 10 |
| MHV-11: | 5'ATGGATTTTGGGCTGATTTTTTTTATTG 3' | 11 |
| MHV-12: | 5'ATGATGGTGTTAAGTCTTCTGTACCTG 3' | 12 |

NB KEY
R = A/G,
Y = T/C,
W = A/T,
K = T/G,
M = A/C,
S = C/G.

TABLE 2

Oligonucleotides primers for the 5' region of Mouse Kappa Variable (MKV) domains.

| | | SEQ ID NO:1 |
|---|---|---|
| MKV-1: | 5'ATGAAGTTGCCTGTTAGGCTGTTGGTGCTG 3' | 13 |
| MKV-2: | 5'ATGGAGWCAGACACACTCCTGYTATGGGT 3' | 14 |
| MKV-3: | 5'ATGAGTGTGCTCACTCAGGTCCTGGSGTTG 3' | 15 |
| MKV-4: | 5'ATGAGGRCCCCTGCTCAGWTTYTTGGMWTCTTG 3' | 16 |
| MKV-5: | 5'ATGGATTTWCAGGTGCAGATTWTCAGCTTC 3' | 17 |
| MKV-6: | 5'ATGAGGTKCYYTGYTSAGYTYCTGRGG 3' | 18 |
| MKV-7: | 5'ATGGGCWTCAAGATGGAGTCACAKWYYCWGG 3' | 19 |
| MKV-8: | 5'ATGTGGGGAYCTKTTTYCMMTTTTTCAATTG 3' | 20 |
| MKV-9: | 5'ATGGTRTCCWCASCTCAGTTCCTTG 3' | 21 |
| MKV-10: | 5'ATGTATATATGTTTGTTGTCTATTTCT 3' | 22 |

TABLE 2-continued

Oligonucleotides primers for the 5' region of Mouse Kappa Variable (MKV) domains.

| | | SEQ ID NO:1 |
|---|---|---|
| MKV-11: | 5'ATGGAAGCCCCAGCTCAGCTTCTCTTCC 3' | 23 |
| MKV-12: | 5'ATGAAGTTTCCTTCTCAACTTCTGCTC 3' | 24 |

NB KEY
R = A/G,
Y = T/C,
W = A/T,
K = T/G,
M = A/C,
S = C/G.

TABLE 3

Oligonucleotide primers for the 3' ends of mouse VH and VL genes.

| | SEQ ID NO:1 |
|---|---|
| Light chain (MKC): 5'TGGATGGTGGGAAGATG 3' | 25 |
| Heavy chain (MHC): 5'CCAGTGGATAGACAGATG 3' | 26 |

Example 2

Ig Sequences Cloned from the 19/2 Murine Hybridoma

Using the cloning strategy described, supra, PCR products for VH and VL of murine 19/2 were cloned using a commercially available product, and art recognized techniques. For the murine 19/2 VL region, PCR products were obtained using the mouse kappa constant region primer and primers MKV2 and MKV7 (SEQ ID NOS: 14 & 19). For the mouse 19/2 VH region, PCR products were obtained using the mouse gamma 1 constant region primer and primers MHV2, MHV5 and MHV7 (SEQ ID NOS: 2, 5 and 7). Extensive DNA sequencing of the cloned V-region inserts revealed two different light chain sequences and 2 different heavy chain sequences. Pseudogenes for heavy and light chain were amplified and were eliminated by standard sequence analyses. A novel immunoglobulin-coding sequence was determined for both the heavy and light chains. This is set forth at SEQ ID NOS: 27, 28, 29 & 30, which present the cDNA and amino acid sequences for the murine 19/2 heavy chain variable region (27 & 28), and the light chain variable region (29 & 30).

Example 3

Mouse 19/2 Heavy Chain Leader Sequence

When comparing the DNA sequence of the leader sequence for 19/2 heavy chain obtained with the primers described supra, with the database, it appeared that the 19/2 HC leader sequence is short (17 amino acids) and unique vis a vis public data bases. Specifically, amino acids 2, 3 and 5 were E, L & M, as compared to S, W & F in the data bases. As compared to the database, hydrophilic amino acids in the N-terminal region were separated by neutral or basic ones, respectively; however, since the influence of these changes on the secretory capability of the leader sequence is unclear, this sequence was unaltered in further experiments.

Example 4

Construction of Mouse-human Chimeric Genes

The chimeric 19/2 antibody was designed to have the mouse 19/2 VL and VH regions linked to human kappa and gamma-1 constant regions, respectively. PCR primers were used to modify the 5'-and 3'-sequences flanking the cDNA sequences coding for the mouse 19/2 VL and VH regions. PCR primers specific for 19/2 light chain V-region were designed using the sequence of the 19/2 light chain V-region gene obtained. These adapted mouse 19/2 variable regions were then subcloned into mammalian cell expression vectors already containing the human kappa (pREN-Neo vector) or the gamma-1 (pRLN-DHFR vector) constant regions. The vectors employ parts of the human elongation factor 1 □ (EF1 □) promoter/enhancer sequence to efficiently transcribe the light and heavy chains. The vectors also contain an IRES sequence following the multiple cloning site to allow for stringent, bicistronic expression and control of the individual selection marker in CHO cells. This pair of vectors was used in all of the recombinant work described herein, i.e., to manufacture all chimeric antibodies. The expression vectors were designed to have the variable regions inserted as PmeI-BamHI DNA fragments. PCR primers were designed to introduce these restrictions sites at the 5'-(PmeI) and 3'-(BamHI) ends of the cDNAs coding for the V-regions. In addition, the PCR primers were designed to introduce a standard Kozak sequence (Kozak (1987) *Nucleic Acids Res.* 15(20): 8125-8148, incorporated by reference herein in its entirety) at the 5'-ends of both the light and heavy chain cDNAs to allow efficient translation, and to introduce splice donor sites at the 3'-ends of both the light and heavy chain cDNAs for the variable regions to be spliced to the constant regions. The PCR primers used for the construction of the chimeric 19/2 light and heavy chains were as follows: catgtttaaacgccfccaccatgggcttcaagatggagtca (5' end, light chain variable region, SEQ ID NO: 31); agaggatccactcacgtttcagttccacttggtcccag (3' end, SEQ ID NO: 32); catgtttaaacgccgccaccatggagctgatcatgctcttcct (primer for the 5' end of the heavy chain variable region, SEQ ID NO: 33); and agaggatccactcacctgaggagactct-gagagtggt (primer for the 3' end of the heavy chain variable region, SEQ ID NO: 34). The DNA and amino acid sequences of the mouse 19/2 VL and VH regions were adapted for use from the construction of chimeric 19/2 light and heavy chains. The entire DNA sequences of mouse 19/2 light and heavy chains cloned into the eukaryotic expression vectors pREN-Neo and pREN-DHFR, respectively, are set forth as SEQ ID NO: 35 & 36, with the resulting light and heavy chains resulting in chimerized molecules. Specifically, in SEQ ID NO: 35, nucleotides 1357-1752 encode the murine, light chain sequence, with nucleotides 1886-2203 encoding the human kappa region. Within this sequence (1886-2203), a 120 base pair region constituting an intron and splice acceptor site begins at nucleotide 1886. Within SEQ ID NO: 36, nucleotides 1357-1764 encode the murine 9/2 heavy chain constant sequence with a splice donor site. Nucleotides 1839-2825 encode the human IgG1 constant region. Within this sequence, there is a 60 base pair intron region and splice acceptor site which precedes the coding region.

Example 5

The objective of the experiments described herein was to create stable cell lines expressing chimeric 19/2 (c19/2) anti-human GM-CSF monoclonal antibodies (mAb) in CHO (Chinese hamster ovary) DG44 cells and to test the secreted antibody for its binding properties. To do this, the DHFR negative CHO cell line DG044 was used. See Morris et al. (1990) *Gene* 94(2): 289-294; incorporated by reference herein in its entirety). The CHO cells were cultured in RPMI, supplemented with 10% FCS and Hypoxanthine-Thymidine. DNA for transfection was purified from *E. coli* cells using a commercially available product, and the instructions provided therein. All DNA preparations were examined by restriction enzyme digestion. Sequences of chimeric 19/2 mAb variable regions in their respective vectors were confirmed using an ABI PRISM 310 or LICOR Sequencer.

Vectors encoding heavy and light chains of chimeric 19/2 mAbs were co-transfected simultaneously into CHO DG44 cells growing at log phase, using electroporation (270V, 975 uF). Cells were plated in 10 cm dishes and cultured with standard medium. Twenty-four hours later, medium was harvested and replaced by fresh RPMI medium supplemented with 10% dialyzed FCS and 500 ug/mL geneticin. After the initial phase of cell killing was over (7-10 days), GMP-grade methotrexate was added at a concentration of 5 nM and gradually increased to 100 nM over the following weeks. Out-growing colonies were picked and screened for antibody production.

Example 6

PCR Amplification of Variable Chain DNA

CHO DG44 cells were centrifuged in an Eppendorf microcentrifuge, briefly, at full speed, washed once with PBS, and pelleted once again. Genomic DNA was prepared by ethanol precipitation after SDS lysis and Proteinase K treatment of the cell pellets.

A mixture containing one of the primer pairs described supra, dNTPs, buffer, and Pfu polymerase was used to amplify either the heavy or light chain variable region using genomic DNA as a template using methods well known in the art. The resulting PCR products were digested with the appropriate restriction enzyme and analysed by agarose gel electrophoresis to confirm their identity.

The primer pairs for the light chain were:

ttcttgaagt ctggtgatgc tgcc, and   (SEQ ID NO:37)

caagctagcc ctctaagactc ctcccctgtt.   (SEQ ID NO:38)

For the light chain and SEQ ID NO: 37 plus gaactcgagt catttacccg gagacaggga gag  (SEQ ID NO:39)

for the heavy chain.

The undigested heavy chain PCR product had a predicted size of 1200 base pairs, while the light chain PCR product had a predicted size of 800 base pairs. Identity was verified by restriction enzyme digest with BamHI.

Example 7

Dot-Blot Method for Measuring Assembled IVG1/Kappa Antibody in CHO Cell Supernatants CHO cell lines were transfected with the corresponding plasmids. Geneticin resistant cells were obtained and these cells were further selected for resistance to methotrexate.

Single colonies were picked after amplification and transferred into 24-well plates. Culture supernatant was tested for chimeric IgG 3-4 days later by standard Dot Blot assays.

Figure 2:
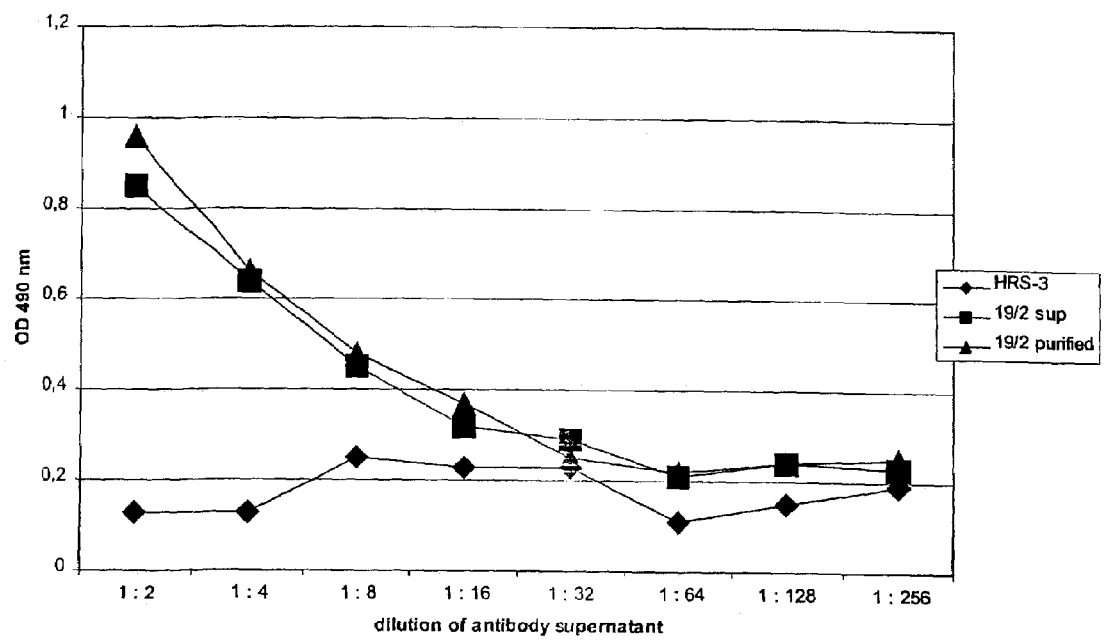
FIG. 2 shows the binding of the antibody via ELISA.

Any positive colonies were sub-cloned and cultured to achieve sufficient antibody production. The chimeric 19/2 antibody was purified from the supernatant on protein G columns and tested for its specific binding with recombinant GM-CSF by Western Blot (FIG. 1) and ELISA (FIG. 2).

Finally, the identity of producer cell lines were confirmed using PCR amplification of both their heavy and light chain variable regions. The DNA sequence of the heavy chain variable region PCR products for chimeric 19/2 mAb transfected cells was confirmed.

Example 8

In order to optimize cell growth and antibody production, the CHODG44/pREN c19/2 cell line was first cultured in commercially available IMDM containing 10% FCS, at 37° C., in a 10% $CO_2$ atmosphere. The cells were then weaned into serum free medium, and cultured in a custom made medium, i.e., IMDM SFII, with the following additives, at 37° C., in a 10% $CO_2$ atmosphere.

|  | Final Concentration |
| --- | --- |
| Base IMDM Medium | |
| Pluronic F68 | 1.0 mg/ml |
| Hypep 4601 | 1.0 mg/ml |
| Hypep 4605 DEV | 0.5 mg/ml |
| HEPES | 5.958 mg/ml |
| $Na_2HCO_3$ | 3.024 mg/ml |
| Additives | |
| Dextran sulfate | 50.0 µg/ml |
| Putrescine | 100.0 nM |
| Albumax I | 2.0 mg/ml |
| Choline chloride | 1.0 mg/ml |
| Trace elements | |
| $FeSO_4 \cdot 7H_2O$ | 0.8 µg/ml |
| $ZnSO_4 \cdot 7H_2O$ | 1.0 µg/ml |
| $CuSO_4 \cdot 5H_2O$ | 0.0025 µg/ml |
| $C_6H_5FeO_7 \cdot H_2O$ | 5.0 µg/ml |
| IGF-1 | 50.0 ng/ml |
| Transferrin | 35.0 µg/ml |
| Ethanolamine | 50.0 µM |
| Mercaptoethanol | 50.0 µM |

Culture supernatants were harvested aseptically, and then clarified by centrifugation. The antibodies were then purified by affinity chromatography on a 5 ml protein. A sepharose fast flow column that had been pre-equilibriated in 50 mM Tris-HCL, pH8, was used. The column was washed, 20 times, with this buffer, and any bound antibody was eluted using 50 mM sodium citrate, pH 3.0, and the eluate was then neutralized, immediately, using 1M Tris-HCl, pH8. Antibodies were concentrated with a centrifugal filter, and dialyzed overnight at 4° C. in PBS. The yield was about 4-5 mg/liter. The purity of the antibodies was examined via SDS-PAGE, under both reducing and non-reducing conditions, using a 4-20% gradient on the SDS-PAGE.

Purified antibodies migrated as a single band under non-reducing conditions, and separated into the heavy and light chains, as expected, under reducing conditions.

The antibodies were also analyzed via size exclusion chromatography, (0.5 mg/ml), on a precalibrated HPLC column. Running buffer (5% n-propanol/PBS (0.5 M phosphate, 0/25 M NaCl, pH 7.4)) was used, at a flow rate of 0.2 ml/min at a temperature of 22° C., which is ambient column temperature.

The analysis demonstrated the integrity of the antibodies, which had calculated molecular weights of 179 kilodaltons.

Example 9

The experiments described in this example were designed to determine the binding activity of the antibodies.

Biosensor analyses were carried out using a commercially available, BIAcore 2000, and a carboxymethyldetran coated sensor chip. The chip was derivatized with 1000, 300, or 100 RVs of recombinant human GM-CSF, on channels 1, 2, and 3 of the machine using standard amine coupling chemistry with channel 4 retained as the control blank channel.

Samples of the chimeric antibody were diluted in HBS buffer (10 mM HEPES, pH7.4, 150 mM NaCl, 3.4 mM di-NA-EDTA, 0.005% Tween-20), and aliquots were injected over the sensor chip at a flow rate of 1 µl/min. After injection, dissociation was monitored by allowing HBS buffer to flow over the chip surface for 5 minutes. Any bound antibody was then eluted, and the chip surface was regenerated, between samples, via injecting 40 µl of 100 mM HCl, pH 2.7, at a rate of 5 µl/min. In order to carry out kinetic analyses of the binding of the chimeric antibody, varying concentrations, ranging from 1-10 nM, were injected over the chip surface, and both apparent association ("Ka") and dissociation ("Kd") rate constants were calculated, using a Langmuir 1:1 binding model, with global and local fitting for calculation of Rmax, using B1Aevaluation V3.1 software.

The results indicated that the chimeric antibody had slightly higher affinity for rhGM-CSF than the murine antibody. The calculated Ka for the chimeric antibody was $5.1 \times 10^5 M^{-1} s^{-1}$ using 100 RU of GM-CSF. No dissociation was observed, regardless of analyte concentration, precluding Kd determination and indicating very high affinity.

Global fitting of Rmax, using the software referred to, gave an off rate of $Kd=1.9 \times 10^{-5} s^{-1}$ and a high affinity for the chimeric antibody of $2.69 \times 10^{10} M^{-1}$.

Example 10

These experiments were designed to determine both the binding activity of the antibodies, and if they cross-reacted with each other.

Nunc plates were coated with recombinant human GM-CSF (1 µg/ml), in carbonate buffer (pH 9.6, 0.05 M), 50 µl/well, and were incubated at 4° C., overnight, and were then blocked with 3% FCS/PBS at room temperature, for one hour.

Half-log, serially diluted triplicate 100 µl samples of either murine or chimeric antibody (10 µg/ml) were added to each well, to yield final concentrations of from 1.0 ng/ml to 10 µg/ml. Following incubation for 1 hour at room temperature, either goat antimouse IgG or antihuman IgG, labelled with horseradish peroxidase (10 ul/well Fe specific; 1:1000 dilution in 1% FCS/PBS) were used to detect bound antibody. After extensive washings, the bound antibodies were visualized by the addition of ABTS substrate (100 µl/well).

Optical density was read at 415 nm in a microplate reader.

The same protocol for binding antibody to the solid phase was used to determine if the antibodies competed with each other. As in the experiments, supra, half-log, serially diluted 100 µl samples, in triplicate, of 10 µg/ml of the murine or chimeric antibody were combined with 20 µg/ml of competing antibody, and then 100 ml of the mixture was added to the coated ELISA plates. Incubation was as above, and anti-murine or anti-human IgG labelled with horseradish peroxidase was used, also as described supra.

The results indicated that the antibodies did compete for binding for recombinant human GM-CSF. A shift in the binding curve was effected by addition of the excess, competing antibody. This indicated binding to, and competition for, a common epitope.

Example 11

These experiments were designed to test the neutralizing activity of the anti-GM-CSF antibodies. Two human GM-CSF dependent cell lines, i.e., TF-1 and AML-193 were used. Growth curves were established, in the presence or absence of 0.5 ng/ml of recombinant human GM-CSF, and viable cell numbers were determined, via Trypan Blue exclusion, on day 0, 1, 2, 3, 5 and 7.

In a first bioassay, recombinant human GM-CSF, in amounts ranging from 0.0003 ng/ml up to 10 µg/ml, was mixed with anti-human GM-CSF antibodies, at a final concentration of 30 µg/ml, in 96 well, microtitre plates. Either TF-1 or AML-193 cells were added ($10^3$ cells/well), and plates were incubated at 37° C. for 7 days.

After this incubation period, the DNA proliferation marker MTS was added, at 20 µl/well. Dye incorporation was measured after 2 hours, by measuring light absorbance at $A_{490\ nm}$.

Increased MTS dye incorporation was observed as the amount of rhGM-CSF in the medium increased. Total growth inhibition of both cell types was observed with the chimeric antibody when rhGM-CSF concentration was 0.1 ng/ml or less, and there was marked inhibition of cell growth at 0.3-10 ng/ml rhGM-CSF.

Figure 3:
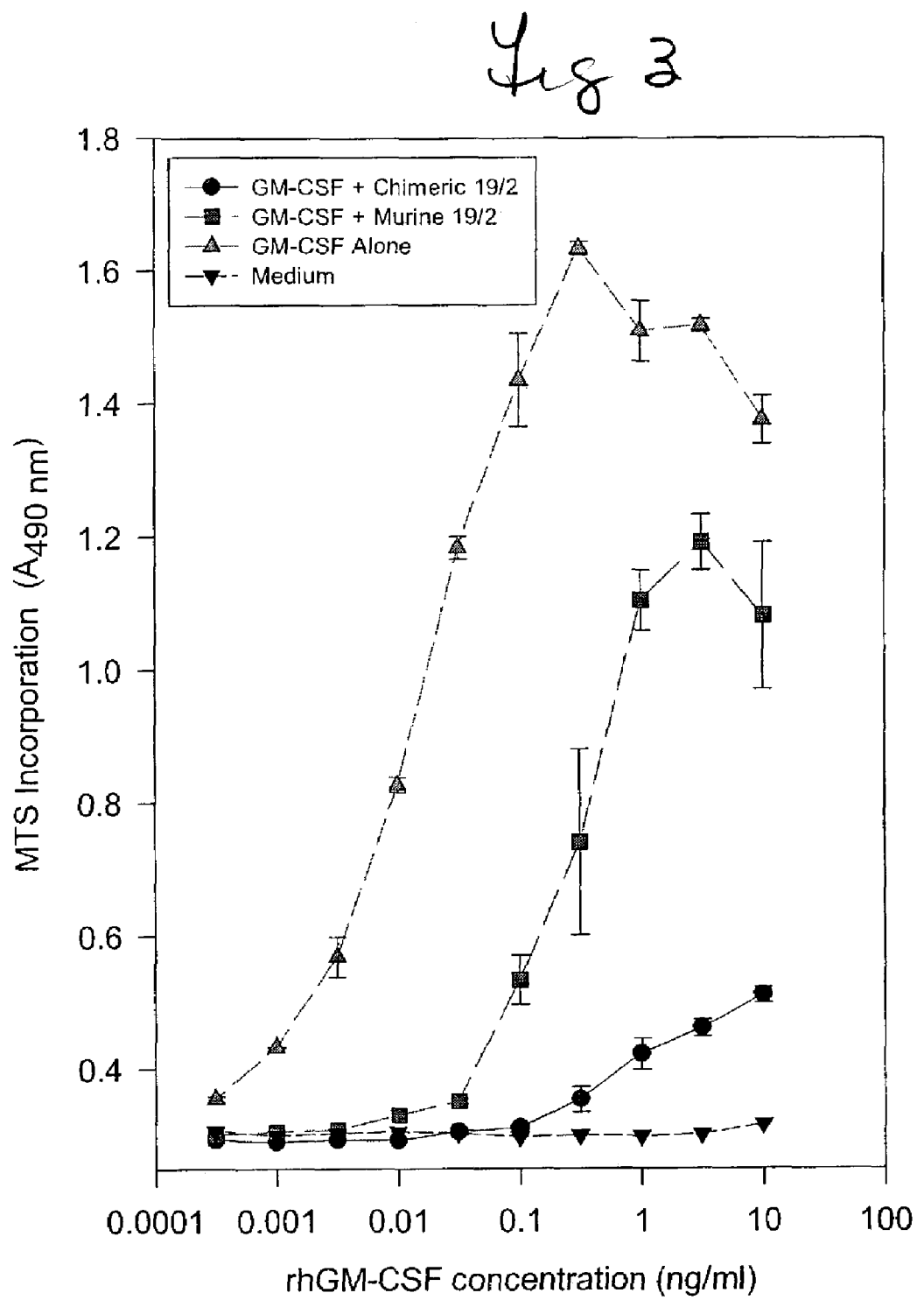
FIG. 3 shows the blocking effect of the antibody on GM-CSF growth dependent TF-1 cells.
Figure 4:
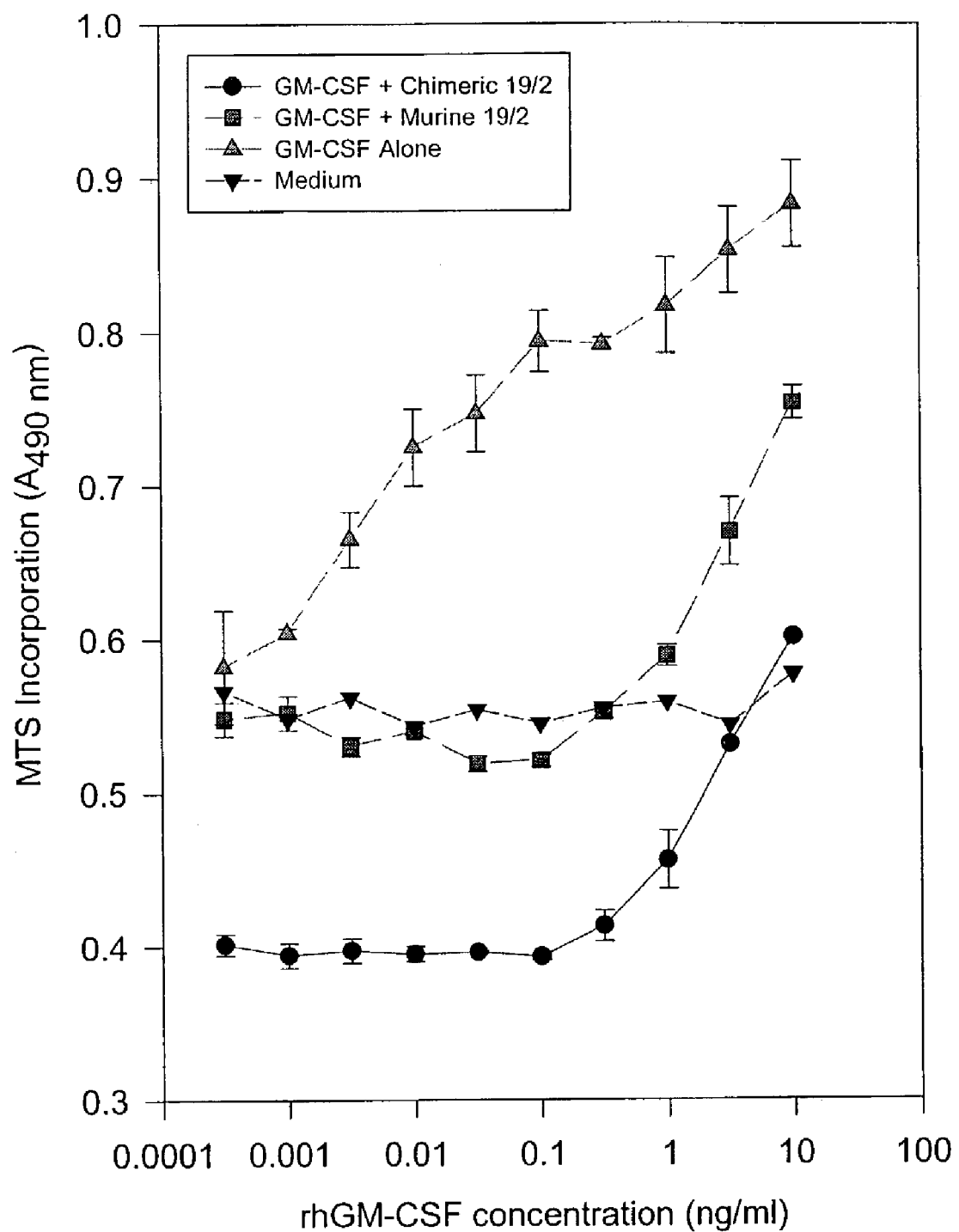
FIG. 4 shows the blocking effect of the antibody on GM-CSF growth dependent AML-193 cells.

In contrast, while the murine antibody had a similar effect on AML-193 cells, it was less effective on TF-1 cells. These results are seen in FIGS. 3 and 4.

Figure 6:
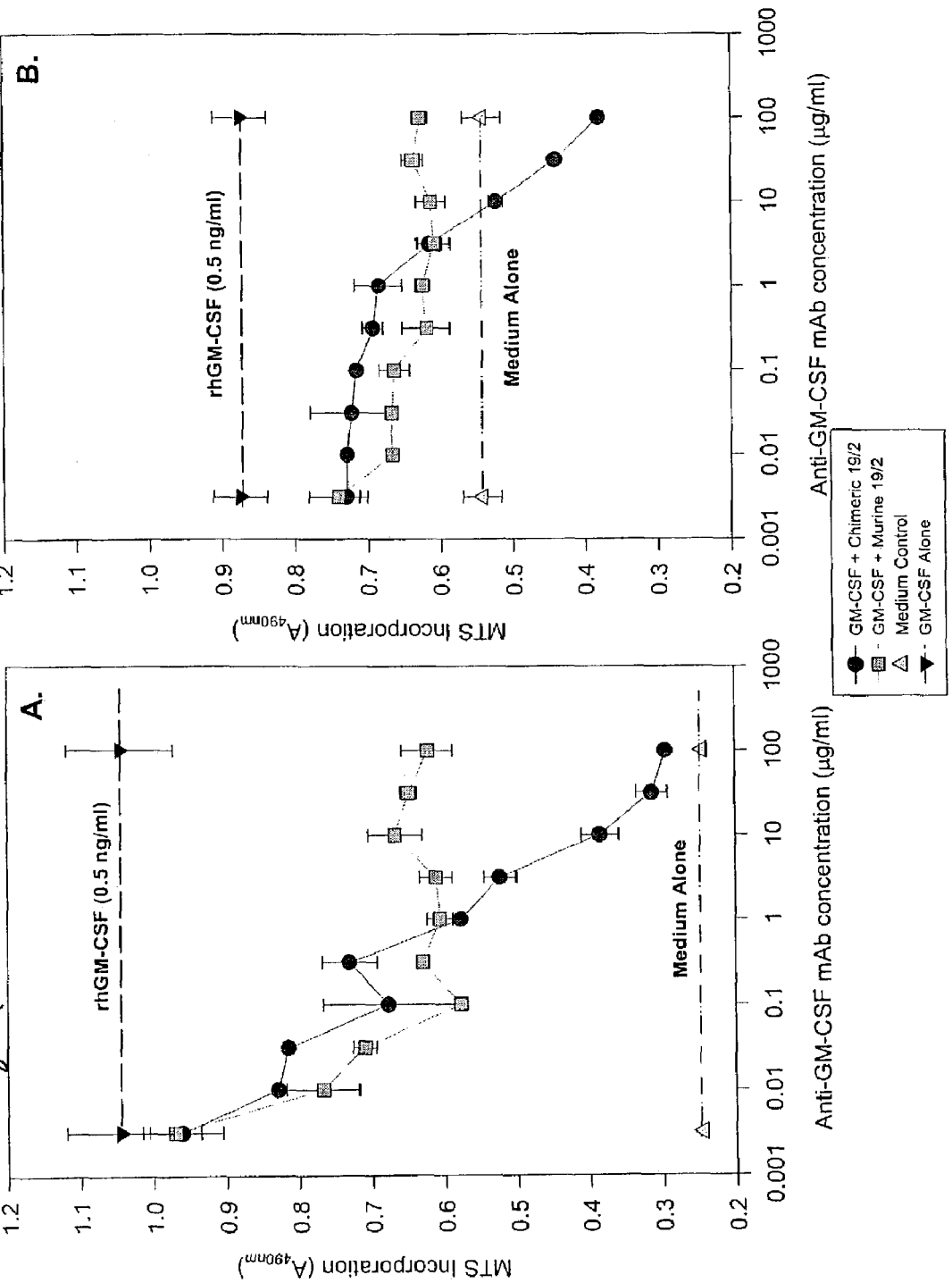
FIG. 6 parallels the experiment of FIG. 5, but uses the AML-153 cells.
Figure 7:
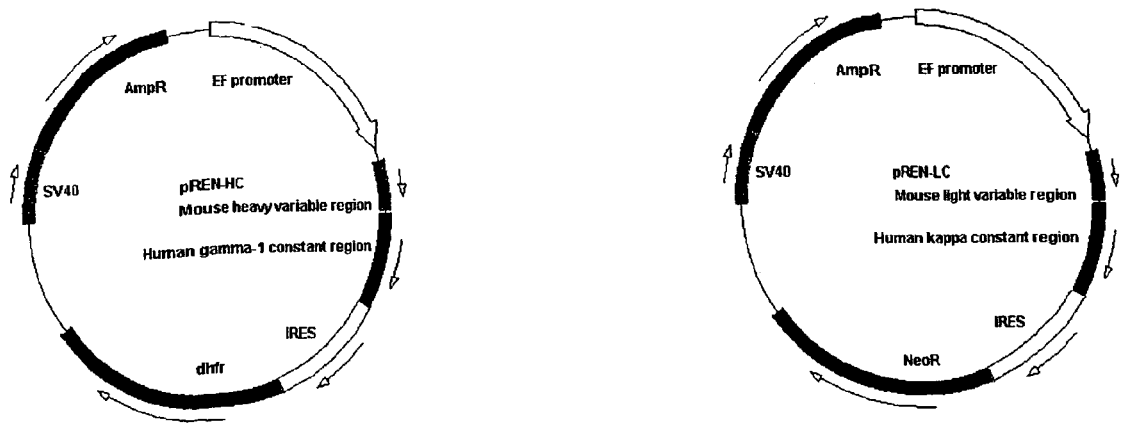
FIG. 7 shows a schematic map of the two expression vectors used to prepare the recombinant antibodies.

In a second bioassay TF-1 and AML-193 cells were grown in the presence of 0.5 ng/mL rhGM-CSF and increasing amounts of murine or chimeric 19/2 mAbs (0.003-100 µg/mL) were added to the culture media and the neutralizing activity assessed after 7 days culture. Results are shown in FIGS. 5 and 6 for the TF-1 and AML-193 cells, respectively. In agreement with the initial bioassay, the chimeric 19/2 demonstrated marked neutralizing activity of GM-CSF stimulated cell growth. A direct correlation was observed between increasing ch19/2 concentration and GM-CSF neutralizing activity plateaued at 3 µg/mL for both cell lines, with higher concentrations unable to effect a greater reduction in TF-1 or AML-193 cell growth. These observations may be due to lower affinity of the murine mAb or steric hindrance at the binding site on GM-CSF.

Example 12

Additional experiments were carried out to produce a chimeric, HRS-3 antibody. The murine form of this antibody is described by Hombach, et al, Int. J. Cancer 55:830-836 (1993), incorporated by reference. The murine antibody binds to CD-30 molecules.

The protocols set forth for production of chimeric, anti GM-CSF antibody set forth supra were used. Since the antibodies were different, and sequences were known, however, different primers were used. These primers serve to introduce splice sites into the cDNA sequences encoding the murine heavy chain and light chain variable regions, and are set forth at SEQ ID NOS: 44, 45, 46 & 47, with SEQ ID NOS: 44 & 45 the nucleotide and amino acid sequences of the heavy chain, and 46 & 47 comparable sequences for the light chain The primers were:

```
                                              (SEQ ID NO:40)
gcgccatggc ccaggtgcaa ctgcagcagt ca and (SEQ ID NO:41)
cagggatcca ctcacctgag gagacggtga ccgt,
``` and for the light chain:

```
                                      (SEQ ID NO:42)
agcgccatgg acatcgagct cactcagtct cca and
                                      (SEQ ID NO:43)
cagggatcca actcacgttg atttccagct tggt.
```

Following amplification, the murine heavy and light chain variable regions were cloned into the pREN Neo and pREN-DHFR sequences, which are set forth at SEQ ID NOS: 48 & 49, respectively. The cloning was possible because the amplification introduced PmeI and BamHI restriction sites into SEQ ID NO: 46, at nucleotides 1-8, and the final 6 nucleotides. Comparable sites are found at nucleotides 1340-1348, and 1357-1362 of SEQ ID NO: 48. Similarly, PmeI and BamHI restriction sites were introduced at nucleotides 1-8, and the last 6 nucleotides of SEQ ID NO: 44, such that this nucleotide sequence could be cloned into SEQ ID NO: 49, at positions 1337-1344, and 1349-1354.

The chimeric HRS-3 antibody was designed to have murine HRS-3 VL and VH regions linked to human kappa and gamma-1 constant regions, respectively. PCR primers were used to modify the 5'- and 3'-sequences flanking the cDNA sequences coding for the murine HRS-3 VL and VH regions. Modification included the insertion of a NcoI site at the 5' primer end and a splice donor site followed by a BamHI restriction site at the 3'-end of both the light and heavy chain cDNAs for the variable regions to be spliced to the constant regions. These adapted mouse HRS-3 variable regions were then subcloned through the NcoI/BamHI restriction sites into a prokaryotic vector harboring a 5'PmeI site followed by a 5' Kozak sequence and by a human antibody leader sequence. Sequences were cut from the prokaryotic vector by PmeI/BamHI digest and subcloned into mammalian cell expression vectors already containing the human kappa (pREN-Neo vector) or gamma-1 (pREN-DHFR vector) constant regions, described supra.

Example 13

Once the constructs were established, they were transfected into DGO44 cells, as described supra.

Positive colonies were sub-cloned, cultured to achieve sufficient antibody production, after which the antibodies were purified, on protein G columns via the Fc fragment.

The purified antibodies were analyzed via SDS-PAGE, following Laemmli, Nature 227:680-5 (1970), as modified by Renner, et al, Eur. J. Immunol 25:2027-35 (1995), incorporated by reference. Samples from different stages of purification were diluted, in either reducing or non-reducing buffer, and were separated on 10-12% polyacrylamide gel via electrophoreses followed by standard Coomassic staining.

The results were in accordance with production of a complete, chimeric antibody, as evidenced by the banding patterns found in both reducing and non-reducing solutions.

Example 14

The binding capacity of the chimeric HRS-3 antibody was determined via flow cytometry, in accordance with Renner, et al, supra. In brief, $1 \times 10^6$ cells of a target tumor line which expressed CD-30 were washed, twice, in PBS, and then incubated with varying concentration of antibody, at 4° C., for 30 minutes. The cells were then washed, and incubated with a secondary antibody, which was directed to the light chain, conjugated to either FITC or PE.

The results indicated that there was weak binding from cell culture supernatant purified from transfected CHO cells, and string binding with purified antibody. No binding was found when CD-30 negative tumor cells were used.

Example 15

The antibody dependent cellular toxicity (ADCC), and the complement dependent toxicity of the chimeric HRS-3 antibody were determined using a europium released assay, as described by Hombach, et al, supra, and Renner, et al, supra.

In brief, for the ADCC assay, peripheral blood lymphocytes were isolated from tow healthy donors, and used at an effector:target ratio of 10:1, with 10,000 europium labelled, CD-30 antigen positive L540CY tumor cells. Antibody was added at varying concentrations (10, 1, 0.1 and 0.01 µg/ml), as was a control of 0 µg/ml. The effect was compared to the murine antibody, a bispecific murine anti-CD16/CD30 antibody, and an irrelevant, chimeric IgG1 antibody. A CD30 negative line was also used. Maximum lysis was measured after 0.025% Triton was added, and all assays were carried out in triplicate.

The results indicated that the chimeric antibody performed better in the ADCC than the murine antibody.

In the CDC assays, 10,000 europium labelled cells (100 µg) (L540Y), were incubated with 50, 5, 0.5, or 0.05 µg/ml antibody in a 50 µl volume. Freshly isolated complement (50 µl) was added, and the mixture was incubated for 2 hours, at 37° C. The murine antibody was also tested, as was an anti CD-16 antibody and a chimeric anti IgG antibody, which served as controls, as did a CD-30 negative cell.

As in the ADCC assay the chimeric antibody was superior in terms of percent lysis to all other antibodies tested.

Example 16

This example details the production of a fusion protein of a chimeric, G250 specific antibody, and tumor necrosis factor ("TNF" hereafter).

G250 is an antigen also now as "carbonic anhydrase 9," or "CA9," or "MN." The G250 antigen and the corresponding antibody was described as being associated with renal cancer carcinoma by Oosterwijk, et al, PCT/US88/01511. The G250 antibody has also been the subject of several clinical trials (Oosterwijk, et al., Int. J. Cancer Oct. 15, 1986: 38(4):489-494; Divgi, et al., Clin. Cancer Res. Nov. 4, 1998(11):2729-739.

Zavada, et al, have issued a series of patents in which the G250 antigen is referred to as "MN" or "MN/CAIX." See, e.g., U.S. Pat. Nos. 6,051,226; 6,027,887; 5,995,075, and 5,981,711, all of which are incorporated by reference. These parents provide details on the antigen, and describe various tumors in which it is found, including cervical cancer, bladder cancer, mammary carcinoma, uterine, cervical, ovarian, and endometrial cancer.

Recently, Ivanov, et al, Am. Journal of Pathology 158(3): 905-919 (2001), conducted investigations of CA9 and CA12 on tumor cells, and cell lines.

cDNA sequences for the light and heavy variable regions of a murine G250 specific antibody are known, and these include the endogenous antibody leader sequence. PCR primers were used to modify both the 5and 3' regions, in order to introduce restriction sites necessary for the introduction of the coding sequences to the vectors employed, which were SEQ ID NOS: 48 & 49, supra. The cDNA sequence which encodes the murine G250 heavy chain variable region is set forth at SEQ ID NO: 50, with the amino acid sequence at SEQ ID NO: 51 and the light chain variable region, at SEQ ID NO: 52, with amino acid sequence at SEQ ID NO: 53. The first 8 nucleotides in each of SEQ ID NOS 50 & 52 represent a PmeI restriction site. The first 19 amino acids encoded by the nucleotide sequence represent the leader region, and the first 24 the leader sequence for the light chain. The last 6 nucleotides in each of SEQ ID NOS: 50 & 52 are a BamHI restriction site. The same protocol as was used for the HRS-3 chimera was used to splice these variable regions into SEQ ID NOS: 48 & 49.

To secure the cDNA encoding human TNF, a human leukocyte cDNA library was used. The peripheral blood lymphocytes were stimulated with PMA, and the cDNA for TNF was amplified, using standard methods. Restriction sites were introduced in the cDNA sequence, so that the cDNA for TNF was positioned right after the hinge region of the G250 heavy chain. A (Gly) Ser coding sequence linked the two. SEQ ID NOS: 54 & 55 set forth the nucleotide and amino acid sequences of a TNF fragment, and SEQ ID NO: 56, a construct wherein the human gamma-1 heavy chain is followed by the TNF coding sequence, right after the IgG1 hinge region.

Within SEQ ID NO: 56, nucleotides 1419-1754 encode a partial, human IgG1 constant region, containing the CH1 and hinge domain, preceded by a 60 base pair intron region and splice acceptor site. The linker, i.e., $(Gly)_4Ser$ is encoded by nucleotides 1755-1769. The coding sequence for the human TNF fragment is set forth at nucleotides 1776-2296.

The resulting constructs were transfected into host cells, as described supra, and expressed. Note that SEQ ID NO: 56 contains a variant of the heavy chain vector noted supra, as it contains the human CH1 and hinge regions, followed by the TNF encoding sequence.

Cells were transfected and cultured as described supra for the HRS-3 chimera, and amplification was carried out using the primers of SEQ ID NOS: 40-43, described supra. The predicted size of the amplification product was 1100 base pairs, and this was in fact confirmed.

Positive colonies were then sub-cloned and cultured, as described supra. The chimeric G250-TNF fusion proteins were purified using anion exchanged chromatography on DEAE columns, using 5 ml samples, and increased salt concentrations in the elution buffer (NaCl, 0→0.5 M) (pH 8). The purity of the fusion proteins was determined, on SDS-PAGE, under reducing conditions. Two bands, of 45 and 28 kDa, respectively, appeared, consistent with the production of a chimeric fusion protein.

The purity of the chimeric fusion protein was confirmed in a sandwich ELISA. In brief, plates were coated with 1:6000 dilutions of affinity purified, goat anti-human IgG serum, and incubated overnight. They were then blocked with 2% gelatin. Either cell culture supernatant, or purified antibody was added, at varying concentrations, and then contacted with biotinylated goat anti-human TNFα specific serum, at 0.1 µg/ml, followed by visualization with a standard streptavidin peroxidase reagent.

The ELISA confirmed the purity of the antibody.

Example 17

FACS was carried out, as described supra for the chimeric HRS-3 antibodies, this time using the fusion protein, and G250 positive tumor cells. Two different purification runs were tested, with chimeric G250 antibody as a positive control, and an irrelevant chimeric IgG1 antibody as a negative control.

The results indicated that the chimeric fusion protein bound as well as the chimeric antibody did. No binding was detected when G250 negative cells were used.

Example 18

These experiments were designed to determine if the fusion proteins retained the ability of TNF to mediate cell death.

This was accomplished using an MTT assay as described by Renner, et al, Eur. J. Immunol 25:2027-2035 (1995), incorporated by reference, and TNF sensitive ("WEHI-R") cells. The WEHI cells were seeded at a density of 10,000 cells/well. Then, after 18 hours, sterile samples of the fusion protein, recombinant TNF, chimeric G250 antibody, or a negative control (plain medium), were added, at concentrations of $1.0 \times 10^5$, $1.0 \times 10^2$, 1, $1.0 \times 10^{-2}$, $1.0 \times 10^{-4}$, and $1.0 \times 10^{-5}$ ng/ml, and the culture was incubated for additional period of from 48-72 hours. Any viable cells were detected, via standard methods, including Annexin V staining, and flow cytometry. To do this, $1 \times 10^6$ WEHI cells were incubated, overnight, with varying antibody concentrations, and dye positive cells were counted. The effect of antibody loaded tumor cells in WEHI killing was determined by pre-staining with commercially available PKH-26GL dye.

The chimeric fusion proteins were found to be as effective as recombinant TNF in killing cells.

Example 19

It is known that TNF stimulates $H_2O_2$ release by human leukocytes. The chimeric fusion proteins were tested for this property.

Granulocytes were isolated from blood samples via standard methods, and were resuspended in reaction buffer (KRPG=145 mM NaCl, 5 mM $Na_2HPO_4$, 4.8 mM KCl, 0.5 mM $CaCl_2$, 1.2 mM $MgSO_4$, 0.2 mM glucose, pH 7.35). This mix was added plates that had been precoated with fibronectin (1 µg/ml, 2 hours, 37° C.) to permit granulocyte adherence. Following this, 100 µl of a dye solution (10 ml KRPG+50 µl A6550+10 µl horseradish-peroxidase) were added and incubated for 15 minutes at 37° C. Granulocytes were added, at 30,000 cells per well, and then either buffer (KRPG), PMA (5 ng/ml), the chimeric fusion protein (1 µg/ml) plus recombinant human IFN-γ (100 µ/ml), or the fusion protein plus the recombinant IFN-γ (at the indicated concentrations), were added. $H_2O_2$ release was measured for 3 hours, using standard methods.

The PMA served as a positive control. The chimeric fusion protein induced $H_2O_2$ release significantly higher than antibody alone, and the $H_2O_2$ release increases even more when IFN-γ was added.

We claim:

1. A chimerized GM-CSF specific antibody consisting of a light chain, the amino acid sequence of which consists of, in N terminal to C terminal order, the amino acids encoded by nucleotides 1357-1752 of SEQ ID NO: 35, followed by the amino acid sequence encoded by nucleotides 1886-2203 of SEQ ID NO: 35, and a heavy chain, the amino acid sequence of which consists of, in N terminal to C terminal order, the amino acids encoded by nuoleotides 1357-1764 of SEQ ID NO: 36, followed by the amino acid sequence encoded by nucleotides 1839-2825 of SEQ ID NO: 36, wherein said chiinerized GM-CSF specific antibody inhibits TF-1 cell growth by more than 50% at a concentration of 10 µg/ml in the presence of 0.5 ng/ml recombinant human GM-CSF.

2. A chimerized, GM-CSF specific antibody comprising a chimeric light chain encoded by an isolated nucleic acid molecule, the amino acid sequence of which consists of, in N terminal to C-terminal order, the amino acids encoded by nucleotides 1357-1742 of SEQ ID NO: 35 followed by the amino acid sequence encoded by nucleotides 1886-2203 of SEQ ID NO: 35.

3. A chimerized, GM-CSF specific antibody comprising a chimeric heavy chain encoded by an isolated nucleic acid molecule, the nucleotide sequence of which consist of in N-terminal to C-terminal order, the amino acids encoded by nucleotides 1357-1764 of SEQ ID NO: 36, followed by the amino acid sequence encoded by nucleotides 1839-2825 of SEQ ID NO: 36.

* * * * *

SEQUENCE LISTING

```
<160> NUMBER OF SEQ ID NOS: 56

<210> SEQ ID NO 1
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 1
atgaaatgca gctgggtcat sttcttc                                           27

<210> SEQ ID NO 2
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 2
atgggatgga gctratcats ytctt                                             25

<210> SEQ ID NO 3
<211> LENGTH: 27
<212> TYPE: DNA
<213> ORGANISM: Artificial Sequence
<220> FEATURE:
<223> OTHER INFORMATION: Oligonucleotide primer
```

<400> SEQUENCE: 3
atgaagwtgt ggttaaactg ggttttt                                27

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 4
atgractttg wytcagcttg rttt                                   24

<210> SEQ ID NO 5
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 5
atggactcca ggctcaamag ttttcctt                               28

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 6
atggctgtcy trgsgctrct cttctgc                                27

<210> SEQ ID NO 7
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 7
atggratgga gckggrtctt tmtctt                                 26

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 8
atgagagtgc tgattctttt gtg                                    23

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 9
atggmttggg tgtggamctt gctattcctg                             30

<210> SEQ ID NO 10
<211> LENGTH: 27

```
<212> TYPE: DNA
<213> ORGANISM: Artificial Sequence
<220> FEATURE:
<223> OTHER INFORMATION: Oligonucleotide primer

<400> SEQUENCE: 10
atgggcagac ttacattctc attcctg                                        27

<210> SEQ ID NO 11
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 11
atggattttg ggctgatttt ttttattg                                       28

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 12
atgatggtgt taagtcttct gtacctg                                        27

<210> SEQ ID NO 13
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 13
atgaagttgc ctgttaggct gttggtgctg                                     30

<210> SEQ ID NO 14
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 14
atggagwcag acacactcct gytatgggt                                      29

<210> SEQ ID NO 15
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 15
atgagtgtgc tcactcaggt cctggsgttg                                     30

<210> SEQ ID NO 16
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 16
```

-continued

| | |
|---|---|
| atgaggrccc ctgctcagwt tyttggmwtc ttg | 33 |

<210> SEQ ID NO 17
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 17

| | |
|---|---|
| atggatttwc aggtgcagat twtcagcttc | 30 |

<210> SEQ ID NO 18
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 18

| | |
|---|---|
| atgaggtkcy ytgytsagyt yctgrgg | 27 |

<210> SEQ ID NO 19
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 19

| | |
|---|---|
| atgggcwtca agatggagtc acakwyycwg g | 31 |

<210> SEQ ID NO 20
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 20

| | |
|---|---|
| atgtgggay ctktttycmm tttttcaatt g | 31 |

<210> SEQ ID NO 21
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 21

| | |
|---|---|
| atggtrtccw casctcagtt ccttg | 25 |

<210> SEQ ID NO 22
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 22

| | |
|---|---|
| atgtatatat gtttgttgtc tatttct | 27 |

<210> SEQ ID NO 23
<211> LENGTH: 28
<212> TYPE: DNA
<213> ORGANISM: Artificial Sequence

```
<220> FEATURE:
<223> OTHER INFORMATION: Oligonucleotide primer

<400> SEQUENCE: 23
atggaagccc cagctcagct tctcttcc                                          28

<210> SEQ ID NO 24
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 24
atgaagtttc cttctcaact tctgctc                                           27

<210> SEQ ID NO 25
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 25
tggatggtgg gaagatg                                                      17

<210> SEQ ID NO 26
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 26
ccagtggata gacagatg                                                     18

<210> SEQ ID NO 27
<211> LENGTH: 456
<212> TYPE: DNA
<213> ORGANISM: Mus musculus
<220> FEATURE:
<223> OTHER INFORMATION: murine 19/2 heavy chain variable region

<400> SEQUENCE: 27
atggagctga tcatgctctt cctcctgtca ggaactgcag gcgtccactc                  50
tgaggtccag cttcagcagt caggacctga actggtgaaa cctggggcct                 100
cagtgaagat atcctgcaag gcttctggat acactttcac tgactacaac                 150
atacactggg tgaaacagag ccatggaaag agccttgact ggattggata                 200
tattgctcct acagtggtg gtactggtta caaccaggag ttcaagaaca                  250
gggccacatt gactgtagac aaatcctcca gcacagccta catggagctc                 300
cgcagtctga catctgatga ctctgcagtc tattactgtg ctagacgaga                 350
ccgtttccct tattactttg actactgggg ccaaggcacc cctctcacag                 400
tctcctcagc caaaacgaca ccccccatctg tctatccact ggcaagggcg                450
aattcc                                                                 456

<210> SEQ ID NO 28
<211> LENGTH: 139
<212> TYPE: PRT
<213> ORGANISM: Mus musculus
<220> FEATURE:
```

<223> OTHER INFORMATION: amino acid sequence for murine 19/2 heavy chain
    variable region

<400> SEQUENCE: 28

Met Glu Leu Ile Met Leu Phe Leu Leu Ser Gly Thr Ala Gly Val His
                5                  10                  15

Ser Glu Val Gln Leu Gln Gln Ser Gly Pro Glu Leu Val Lys Pro Gly
            20                  25                  30

Ala Ser Val Lys Ile Ser Cys Lys Ala Ser Gly Tyr Thr Phe Thr Asp
        35                  40                  45

Tyr Asn Ile His Trp Val Lys Gln Ser His Gly Lys Ser Leu Asp Trp
    50                  55                  60

Ile Gly Tyr Ile Ala Pro Tyr Ser Gly Gly Thr Gly Tyr Asn Gln Glu
65                  70                  75                  80

Phe Lys Asn Arg Ala Thr Leu Thr Val Asp Lys Ser Ser Thr Ala
                85                  90                  95

Tyr Met Glu Leu Arg Ser Leu Thr Ser Asp Asp Ser Ala Val Tyr Tyr
            100                 105                 110

Cys Ala Arg Arg Asp Arg Phe Pro Tyr Phe Asp Tyr Trp Gly Gln Gly
        115                 120                 125

Thr Thr Leu Arg Val Ser Ser Val Ser Gly Ser
    130                 135

<210> SEQ ID NO 29
<211> LENGTH: 450
<212> TYPE: DNA
<213> ORGANISM: Mus musculus
<220> FEATURE:
<223> OTHER INFORMATION: murine 19/2 light chain variable region

<400> SEQUENCE: 29
atgggcttca agatggagtc acagatccag gtctttgtat acatgttgct         50
gtggttgtct ggtgttgatg gagacattgt gatgatccag tctcaaaaat        100
tcgtatccac atcagtagga gacagggtca atatcacctg caaggccagt        150
cagaatgtgg gaagtaatgt agcctggttg caacagaaac ctggacaatc        200
tcctaaaacg ctgatttact cggcatcgta ccggtccggt cgagtccctg        250
atcgcttcac aggcagtgga tctggaacag atttcattct taccatcact        300
actgtgcagt ctgaagactt ggcagaatat ttctgtcagc aatttaacag        350
gtctcctctc acgttcggtt ctgggaccaa gttggaactg aaacgggctg        400
atgctgcacc aactgtatcc atcttcccac catccagtaa gggcgaattc        450

<210> SEQ ID NO 30
<211> LENGTH: 150
<212> TYPE: PRT
<213> ORGANISM: Mus musculus
<220> FEATURE:
<223> OTHER INFORMATION: amino acid sequence for murine 19/2 light chain
    variable region

<400> SEQUENCE: 30

Met Gly Phe Lys Met Glu Ser Gln Ile Gln Val Phe Val Tyr Met Leu
                5                  10                  15

Leu Trp Leu Ser Gly Val Asp Gly Asp Ile Val Met Ile Gln Ser Gln
            20                  25                  30

Lys Phe Val Ser Thr Ser Val Gly Asp Arg Val Asn Ile Thr Cys Lys
        35                  40                  45

```
Ala Ser Gln Asn Val Gly Ser Asn Val Ala Trp Leu Gln Gln Lys Pro
    50                  55                  60

Gly Gln Ser Pro Lys Thr Leu Ile Tyr Ser Ala Ser Tyr Arg Ser Gly
 65                  70                  75                  80

Arg Val Pro Asp Arg Phe Thr Gly Ser Gly Ser Gly Thr Asp Phe Ile
                85                  90                  95

Leu Thr Ile Thr Thr Val Gln Ser Glu Asp Leu Ala Glu Tyr Phe Cys
            100                 105                 110

Gln Gln Phe Asn Arg Ser Pro Leu Thr Phe Gly Ser Gly Thr Lys Leu
        115                 120                 125

Glu Leu Lys Arg Ala Asp Ala Ala Pro Thr Val Ser Ile Phe Pro Pro
    130                 135                 140

Ser Ser Lys Gly Glu Phe
145                 150

<210> SEQ ID NO 31
<211> LENGTH: 41
<212> TYPE: DNA
<213> ORGANISM: Artificial Sequence
<220> FEATURE:
<223> OTHER INFORMATION: primer used for the construction of the
      chimeric 19/2 light chain

<400> SEQUENCE: 31 catgttttaaa cgccgccacc atgggcttca agatggagtc a                    41

<210> SEQ ID NO 32
<211> LENGTH: 38
<212> TYPE: DNA
<213> ORGANISM: Artificial Sequence
<220> FEATURE:
<223> OTHER INFORMATION: primer used for the construction of the
      chimeric 19/2 light chain

<400> SEQUENCE: 32
agaggatcca ctcacgtttc agttccactt ggtcccag                         38

<210> SEQ ID NO 33
<211> LENGTH: 43
<212> TYPE: DNA
<213> ORGANISM: Artificial Sequence
<220> FEATURE:
<223> OTHER INFORMATION: primer used for the construction of the
      chimeric 19/2 heavy chain

<400> SEQUENCE: 33 catgttttaaa cgccgccacc atggagctga tcatgctctt cct                  43

<210> SEQ ID NO 34
<211> LENGTH: 37
<212> TYPE: DNA
<213> ORGANISM: Artificial Sequence
<220> FEATURE:
<223> OTHER INFORMATION: primer used for the construction of the
      chimeric 19/2 heavy chain

<400> SEQUENCE: 34
agaggatcca ctcacctgag gagactctga gagtggt                          37

<210> SEQ ID NO 35
<211> LENGTH: 6159
<212> TYPE: DNA
<213> ORGANISM: Artificial Sequence
```

<220> FEATURE:
<223> OTHER INFORMATION: pREN 19/2 LC Neo Vector

<400> SEQUENCE: 35

```
ctcgagagcg gcagtgagc gcaacgcaat taatgtgagt tagctcactc                50
attaggcacc ccaggcttta cactttatgc tcccggctcg tatgttgtgt              100
ggagattgtg agcggataac aatttcacac agaattcgtg aggctccggt              150
gcccgtcagt gggcagagcg cacatcgccc acagtccccg agaagttggg              200
gggaggggtc ggcaattgaa ccggtgccta gagaaggtgg cgcggggtaa              250
actgggaaag tgatgtcgtg tactggctcc gccttttcc cgagggtggg               300 ggagaaccgt atataagtgc agtagtcgcc gtgaacgttc tttttcgcaa              350
cgggtttgcc gccagaacac aggtaagtgc cgtgtgtggt tcccgcgggc              400
ctggcctctt tacgggttat ggcccttgcg tgccttgaat tacttccacg              450
cccctggctg cagtacgtga ttcttgatcc cgagcttcgg gttggaagtg              500
ggtgggagag ttcgaggcct tgcgcttaag gagcccctc gcctcgtgct               550 tgagttgagg cctggcctgg gcgctgggc cgccgcgtgc gaatctggtg               600
gcaccttcgc gcctgtctcg ctgctttcga taagtctcta gccatttaaa              650 attttgatg acctgctgcg acgctttttt tctggcaaga gagtcttgta               700
aatgcgggcc aagatctgca cactggtatt tcggttttg gggccgcggg               750 cggcgacggg gcccgtgcgt cccagcgcac atgttcggcg aggcggggcc              800
tgcgagcgcg gccaccgaga tcggacgggg gtagtctca agctggccgg               850 cctgctctgg tgcctggcct cgcgccgccg tgtatcgccc cgccctgggc              900
ggcaaggctg gcccggtcgg caccagttgc gtgagcggaa agatggccgc              950
ttcccggccc tgctgcaggg agctcaaaat ggaggacgcg cgcgtcggga              1000
gagcgggcgg gtgagtcacc cacacaagg aaaagggcct ttccgtcctc              1050
agccgtcgct tcatgtgact ccacggagta ccgggcgccg tccaggcacc              1100
tcgattagtt ctcgagcttt tggagtacgt cgtctttagg ttgggggag               1150 gggttttatg cgatggagtt tccccacact gagtgggtgg agactgaagt              1200
taggccagct tggcacttga tgtaattctc cttggaattt gccctttttg              1250
agtttggatc ttggttcatt ctcaagcctc agacagtggt tcaaagtttt              1300
tttcttccat ttcaggtgta cgcgtctcgg gaagcttag ttta aaacgcc               1350
```

```
gccacc atg ggc ttc aag atg gag tca cag atc cag gtc ttt              1392
       Met Gly Phe Lys Met Glu Ser Gln Ile Gln Val Phe
                   5                  10 gta tac atg ttg ctg tgg ttg tct ggt gtt gat gga gac att            1434
Val Tyr Met Leu Leu Trp Leu Ser Gly Val Asp Gly Asp Ile
         15                  20                  25 gtg atg atc cag tct caa aaa ttc gta tcc aca tca gta gga            1476
Val Met Ile Gln Ser Gln Lys Phe Val Ser Thr Ser Val Gly
             30                  35                  40 gac agg gtc aat atc acc tgc aag gcc agt cag aat gtg gga            1518
Asp Arg Val Asn Ile Thr Cys Lys Ala Ser Gln Asn Val Gly
                 45                  50 agt aat gta gcc tgg ttg caa cag aaa cct gga caa tct cct            1560
Ser Asn Val Ala Trp Leu Gln Gln Lys Pro Gly Gln Ser Pro
55                  60                  65
```

```
aaa acg ctg att tac tcg gca tcg tac cgg tcc ggt cga gtc      1602
Lys Thr Leu Ile Tyr Ser Ala Ser Tyr Arg Ser Gly Arg Val
 70                  75                  80 cct gat cgc ttc aca ggc agt gga tct gga aca gat ttc att      1644
Pro Asp Arg Phe Thr Gly Ser Gly Ser Gly Thr Asp Phe Ile
         85                  90                  95 ctt acc atc act act gtg cag tct gaa gac ttg gca gaa tat      1686
Leu Thr Ile Thr Thr Val Gln Ser Glu Asp Leu Ala Glu Tyr
                100                 105                 110 ttc tgt cag caa ttt aac agg tct cct ctc acg ttc ggt tct      1728
Phe Cys Gln Gln Phe Asn Arg Ser Pro Leu Thr Phe Gly Ser
                    115                 120 ggg acc aag ttg gaa ctg aaa cgt gagtggatcc atctgggata        1772
Gly Thr Lys Leu Glu Leu Lys Arg
125                 130 agcatgctgt tttctgtctg tccctaacat gccctgtgat tatgcgcaaa       1822
caacacaccc aagggcagaa ctttgttact taaacaccat cctgtttgct       1872
tctttcctca gga act gtg gct gca cca tct gtc ttc atc ttc       1915
              Thr Val Ala Ala Pro Ser Val Phe Ile Phe
                              135                 140 ccg cca tct gat gag cag ttg aaa tct gga act gcc tct gtt      1957
Pro Pro Ser Asp Glu Gln Leu Lys Ser Gly Thr Ala Ser Val
        145                 150                 155 gtg tgc ctg ctg aat aac ttc tat ccc aga gag gcc aaa gta      1999
Val Cys Leu Leu Asn Asn Phe Tyr Pro Arg Glu Ala Lys Val
                160                 165                 170 cag tgg aag gtg gat aac gcc ctc caa tcg ggt aac tcc cag      2041
Gln Trp Lys Val Asp Asn Ala Leu Gln Ser Gly Asn Ser Gln
                    175                 180 gag agt gtc aca gag cag gac agc aag gac agc acc tac agc      2083
Glu Ser Val Thr Glu Gln Asp Ser Lys Asp Ser Thr Tyr Ser
185                 190                 195 ctc agc agc acc ctg acg ctg agc aaa gca gac tac gag aaa      2125
Leu Ser Ser Thr Leu Thr Leu Ser Lys Ala Asp Tyr Glu Lys
        200                 205                 210 cac aaa gtc tac gcc tgc gaa gtc acc cat cag ggc ctg agc      2167
His Lys Val Tyr Ala Cys Glu Val Thr His Gln Gly Leu Ser
                215                 220                 225 tcg ccc gtc aca aag agc ttc aac agg gga gag tgt tga          2206
Ser Pro Val Thr Lys Ser Phe Asn Arg Gly Glu Cys
                    230                 235 gctagaacta actaactaag ctagcaacgg tttccctcta gcgggatcaa       2256
ttccgccccc ccccctaac gttactggcc gaagccgctt ggaataaggc        2306
cggtgtgcgt ttgtctatat gttatttttcc accatattgc cgtcttttgg     2356
caatgtgagg gcccggaaac ctggccctgt cttcttgacg agcattccta       2406
ggggtctttc ccctctcgcc aaaggaatgc aaggtctgtt gaatgtcgtg       2456
aaggaagcag ttcctctgga agcttcttga agacaaacaa cgtctgtagc       2506
gaccctttgc aggcagcgga accccccacc tggcgacagg tgcctctgcg       2556
gccaaaagcc acgtgtataa gatacacctg caaaggcggc acaacccag        2606 tgccacgttg tgagttggat agttgtggaa agagtcaaat ggctctcctc       2656
aagcgtattc aacaaggggc tgaaggatgc ccagaaggta ccccattgta       2706
tgggatctga tctggggcct cggtgcacat gctttacgtg tgtttagtcg       2756
aggttaaaaa acgtctaggc ccccgaacc acggggacgt ggttttcctt       2806
```

-continued

```
tgaaaaacac gataatacca tggttgaaca agatggattg cacgcaggtt         2856
ctccggccgc ttgggtggag aggctattcg gctatgactg ggcacaacag         2906
acaatcggct gctctgatgc cgccgtgttc cggctgtcag cgcaggggcg         2956
cccggttctt tttgtcaaga ccgacctgtc cggtgccctg aatgaactgc         3006
aggacgagcg agcgcggcta tcgtggctgg ccacgacggg cgttccttgc         3056
gcagctgtgc tcgacgttgt cactgaagcg ggaagggact ggctgctatt         3106
gggcgaagtg ccggggcagg atctcctgtc atctcacctt gctcctgccg         3156
agaaagtatc catcatggct gatgcaatgc ggcggctgca tacgcttgat         3206
ccggctacct gcccattcga ccaccaagcg aaacatcgca tcgagcgagc         3256
acgtactcgg atggaagccg gtcttgtcga tcaggatgat ctggacgaag         3306
agcatcaggg gctcgcgcca gccgaactgt tcgccaggct caaggcgcgc         3356
atgcccgacg gcgaggatct cgtcgtgacc catggcgatg cctgcttgcc         3406
gaatatcatg gtggaaaatg gccgcttttc tggattcatc gactgtggcc         3456
ggctgggtgt ggcggaccgc tatcaggaca tagcgttggc tacccgtgat         3506
attgctgaag agcttggcgg cgaatgggct gaccgcttcc tcgtgcttta         3556
cggtatcgcc gctcccgatt cgcagcgcat cgccttctat cgccttcttg         3606
acgagttctt ctgagtcgat cgacctggcg taatagcgaa gaggcccgca         3656
ccgatcgccc ttcccaacag ttgcgcagcc tgaatggcga atgggacgcg         3706
ccctgtagcg cgcattaag cgcggcgggt gtggtggtta cgcgcagcgt         3756
gaccgctaca cttgccagcg ccctagcgcc cgctcctttc gctttcttcc         3806
cttcctttct cgccacgttc gccggctttc ccgtcaagc tctaaatcgg         3856 gggctcccct tagggttccg atttagtgct ttacggcacc tcgaccccaa         3906
aaaacttgat tagggtgatg gttcacgtag tgggccatcg ccctgataga         3956
cggtttttcg ccttttgacgt ggagtccac gttctttaat agtggactct         4006
tgttccaaac tggaacaaca ctcaaccta tctcggtcta tttataaggg         4056
attttgccga tttcggccta ttggttaaaa aatgagctga tttaacaaaa         4106
tttaacgcga attttaacaa aatattaacg cttacaattt aggtggcact         4156
tttcggggaa atgtgcgcgg aaccctata tttgtttatt tttctaaata         4206
cattcaaata tgtatccgct catgagacaa taaccctgat aaatgcttca         4256
ataatattga aaaaggaaga gtatgagtat tcaacatttc cgtgtcgccc         4306
ttattccctt ttttgcggca ttttgcctta ctgttttgc tcacccagaa         4356 acgctggtga aagtaaaaga tgctgaagat cagttgggtg cacgagtggg         4406
ttacatcgaa ctggatctca acagcggtaa gatccttgag agttttcgcc         4456
ccgaagaacg ttttccaatg atgagcactt ttaaagttct gctatgtggc         4506
gcggtattat cccgtattga cgccgggcaa gagcaactcg gtcgccgcat         4556
acactattct cagaatgact tggttgagta ctcaccagtc acagaaaagc         4606
atattacgga tggcatgaca gtaagagaat tatgcagtgc tgccataacc         4656
atgagtgata acactgcggc caacttactt ctgacaacga tcggaggacc         4706
gaaggagcta accgcttttt tgcacaacat ggggggatcat gtaactcgcc         4756
```

| | |
|---|---|
| ttgatcgttg ggaaccggag ctgaatgaag ccataccaaa cgacgagcgt | 4806 |
| gacaccacga tgcctgtagc aatggcaaca acgttgcgca aactattaac | 4856 |
| tggcgaacta cttactctag cttcccggca acaattaata gactggatgg | 4906 |
| aggcggataa agttgcagga ccacttctgc gctcggccct tccggctggc | 4956 |
| tggtttattg ctgataaatc tggagccggt gagcgtgggt ctcgcggtat | 5006 |
| cattgcagca ctggggccag atggtaagcc ctcccgtatc gtagttatct | 5056 |
| acacgacggg gagtcaggca actatggatg aacgaaatag acagatcgct | 5106 |
| gagataggtg cctcactgat taagcattgg taactgtcag accaagttta | 5156 |
| ctcatatata ctttagattg atttaaaact tcatttttaa tttaaaagga | 5206 |
| tctaggtgaa gatcctttt gataatctca tgaccaaaat cccttaacgt | 5256 |
| gagttttcgt tccactgagc gtcagacccc gtagaaaaga tcaaaggatg | 5306 |
| ttcttgagat cctttttttc tgcacgtaat ctgctgcttg caaacaaaaa | 5356 |
| accaccgcta ccagcggtgg tttgtttgcc ggatcaagag ctaccaactc | 5406 |
| tttttccgaa ggtaactggc ttcagcagag cgcagatacc aaatactgtc | 5456 |
| cttctagtgt agccgtagtt aggccaccac ttcaagaact ctgtagcacc | 5506 |
| gcctacatac ctcgctctgc taatcctgtt accagtggct gctgccagtg | 5556 |
| gcgataagtc gtgtcttacc gggttggact caagacgata gttaccggat | 5606 |
| aaggcgcagc ggtcgggctg aacggggggt tcgtgcacac agcccagctt | 5656 |
| ggagcgaacg acctacaccg aactgagata cctacagcgt gagctatgag | 5706 |
| aaagcgccac gcttcccgaa gggagaaagg cggacaggta tccggtaagc | 5756 |
| ggcagggtcg gaacaggaga gcgcacgagg gagcttccag ggggaaacgc | 5806 |
| ctggtatctt tatagtcctg tcgggtttcg ccacctctga cttgagcgtc | 5856 |
| gatttttgtg atgctcgtca gggggggcgga gcctatggaa aaacgccagc | 5906 |
| aacgcggcct ttttacggtt cctggccttt tgctggcctt ttgctcacat | 5956 |
| gttctttcct gcgttatccc ctgattctgt ggataaccgt attaccgcct | 6006 |
| ttgagtgagc tgataccgct cgccgcagcc gaacgaccga gcgcagcgag | 6056 |
| tcagtgagcg aggaagcgga agagcgccca atacgcaaac cgcctctccc | 6106 |
| cgcgcgttgg ccgattcatt aatgcaggta tcacgaggcc ctttcgtctt | 6156 |
| cac | 6159 |

<210> SEQ ID NO 36
<211> LENGTH: 6629
<212> TYPE: DNA
<213> ORGANISM: Artificial Sequence
<220> FEATURE:
<223> OTHER INFORMATION: pREN 19/2 HC DHFR Vector

<400> SEQUENCE: 36

| | |
|---|---|
| ctcgagagcg ggcagtgagc gcaacgcaat taatgtgagt tagctcactc | 50 |
| attaggcacc ccaggcttta cactttatgc tccggctcg tatgttgtgt | 100 |
| ggagattgtg agcggataac aatttcacac agaattcgtg aggctccggt | 150 |
| gcccgtcagt gggcagagcg cacatcgccc acagtccccg agaagttggg | 200 |
| gggaggggtc ggcaattgaa ccggtgccta gagaaggtgg cgcggggtaa | 250 |
| actgggaaag tgatgtcgtg tactggctcc gcctttttcc cgagggtggg | 300 |

-continued

| | |
|---|---|
| ggagaaccgt atataagtgc agtagtcgcc gtgaacgttc tttttcgcaa | 350 |
| cgggtttgcc gccagaacac aggtaagtgc cgtgtgtggt tcccgcgggc | 400 |
| ctggcctctt tacgggttat ggcccttgcg tgccttgaat tacttccacg | 450 |
| cccctggctg cagtacgtga ttcttgatcc cgagcttcgg gttggaagtg | 500 |
| ggtgggagag ttcgaggcct tgcgcttaag gagccccttc gcctcgtgct | 550 |
| tgagttgagg cctggcctgg cgctggggc cgccgcgtgc gaatctggtg | 600 |
| gcaccttcgc gcctgtctcg ctgctttcga taagtctcta gccatttaaa | 650 |
| attttgatg acctgctgcg acgctttttt tctggcaaga tagtcttgta | 700 |
| aatgcgggcc aagatctgca cactggtatt tcggtttttg gggccgcggg | 750 |
| cggcgacggg gcccgtgcgt cccagcgcac atgttcggcg aggcggggcc | 800 |
| tgcgagcgcg gccaccgaga tcggacgggg ggtagtctca agctggccgg | 850 |
| cctgctctgg tgcctggcct cgcgccgccg tgtatcgccc cgccctgggc | 900 |
| ggcaaggctg gccggtcgg caccagttgc gtgagcggaa agatggccgc | 950 |
| ttccccggccc tgctgcaggg agctcaaaat ggaggacgcg gcgctcggga | 1000 |
| gagcgggcgg gtgagtcacc cacacaaagg aaaagggcct ttccgtcctc | 1050 |
| agccgtcgct tcatgtgact ccacggagta ccgggcgccc tccaggcacc | 1100 |
| tcgattagtt ctcgagcttt tggagtacgt cgtctttagg ttgggggag | 1150 |
| gggttttatg cgatggagtt tccccacact gagtgggtgg agactgaagt | 1200 |
| taggccagct tggcacttga tgtaattctc cttggaattt gcccttttg | 1250 |
| agtttggatc ttggttcatt ctcaagcctc agacagtggt tcaaagtttt | 1300 |
| tttcttccat ttcaggtgta cgcgtctcgg gaagctttag tttaaacgcc | 1350 |
| gccacc atg gag ctg atc atg ctc ttc ctc ctg tca gga act | 1392 |
|       Met Glu Leu Ile Met Leu Phe Leu Leu Ser Gly Thr | |
|                  5                10 | |
| gca ggc gtc cac tct gag gtc cag ctt cag cag tca gga cct | 1434 |
| Ala Gly Val His Ser Glu Val Gln Leu Gln Gln Ser Gly Pro | |
|      15             20             25 | |
| gaa ctg gtg aaa cct ggg gcc tca gtg aag ata tcc tgc aag | 1476 |
| Glu Leu Val Lys Pro Gly Ala Ser Val Lys Ile Ser Cys Lys | |
|         30              35             40 | |
| gct tct gga tac act ttc act gac tac aac ata cac tgg gtg | 1518 |
| Ala Ser Gly Tyr Thr Phe Thr Asp Tyr Asn Ile His Trp Val | |
|             45                50 | |
| aaa cag agc cat gga aag agc ctt gac tgg att gga tat att | 1560 |
| Lys Gln Ser His Gly Lys Ser Leu Asp Trp Ile Gly Tyr Ile | |
| 55             60                65 | |
| gct cct tac agt ggt ggt act ggt tac aac cag gag ttc aag | 1602 |
| Ala Pro Tyr Ser Gly Gly Thr Gly Tyr Asn Gln Glu Phe Lys | |
|         70              75             80 | |
| aac agg gcc aca ttg act gta gac aaa tcc tcc agc aca gcc | 1644 |
| Asn Arg Ala Thr Leu Thr Val Asp Lys Ser Ser Ser Thr Ala | |
|            85             90             95 | |
| tac atg gag ctc cgc agt ctg aca tct gat gac tct gca gtc | 1686 |
| Tyr Met Glu Leu Arg Ser Leu Thr Ser Asp Asp Ser Ala Val | |
|              100            105           110 | |
| tat tac tgt gct aga cga gac cgt ttc cct tat tac ttt gac | 1728 |
| Tyr Tyr Cys Ala Arg Arg Asp Arg Phe Pro Tyr Tyr Phe Asp | |
|             115             120 | |

-continued

| | |
|---|---|
| tac tgg ggc caa ggc acc act ctc aga gtc tcc tca gtgagt<br>Tyr Trp Gly Gln Gly Thr Thr Leu Arg Val Ser Ser<br>125                    130                    135 | 1770 |
| ggatcctctg cgcctgggcc cagctctgtc ccacaccgcg gtcacatggc | 1820 |
| accacctctc ttgcagcc tcc acc aag ggc cca tcg gtc ttc<br>                            Ser Thr Lys Gly Pro Ser Val Phe<br>                                          140 | 1862 |
| ccc ctg gca ccc tcc tcc aag agc acc tct ggg ggc aca<br>Pro Leu Ala Pro Ser Ser Lys Ser Thr Ser Gly Gly Thr<br>145                    150                    155 | 1901 |
| gcg gcc ctg ggc tgc ctg gtc aag gac tac ttc ccc gaa ccg<br>Ala Ala Leu Gly Cys Leu Val Lys Asp Tyr Phe Pro Glu Pro<br>          160                    165                    170 | 1943 |
| gtg acg gtg tcg tgg aac tca ggc gcc ctg acc agc ggc gtg<br>Val Thr Val Ser Trp Asn Ser Gly Ala Leu Thr Ser Gly Val<br>                  175                    180                    185 | 1985 |
| cac acc ttc ccg gct gtc cta cag tcc tca gga ctc tac tcc<br>His Thr Phe Pro Ala Val Leu Gln Ser Ser Gly Leu Tyr Ser<br>                      190                    195 | 2027 |
| ctc agc agc gtg gtg acc gtg ccc tcc agc agc ttg ggc acc<br>Leu Ser Ser Val Val Thr Val Pro Ser Ser Ser Leu Gly Thr<br>200                    205                    210 | 2069 |
| cag acc tac atc tgc aac gtg aat cac aag ccc agc aac acc<br>Gln Thr Tyr Ile Cys Asn Val Asn His Lys Pro Ser Asn Thr<br>          215                    220                    225 | 2111 |
| aag gtg gac aag aaa gtt gag ccc aaa tct tgt gac aaa act<br>Lys Val Asp Lys Lys Val Glu Pro Lys Ser Cys Asp Lys Thr<br>                      230                    235                    240 | 2153 |
| cac aca tgc cca ccg tgc cca gca cct gaa ctc ctg ggg gga<br>His Thr Cys Pro Pro Cys Pro Ala Pro Glu Leu Leu Gly Gly<br>                        245                    250                    255 | 2195 |
| ccg tca gtc ttc ctc ttc ccc cca aaa ccc aag gac acc ctc<br>Pro Ser Val Phe Leu Phe Pro Pro Lys Pro Lys Asp Thr Leu<br>                  260                    265 | 2237 |
| atg atc tcc cgg acc cct gag gtc aca tgc gtg gtg gtg gac<br>Met Ile Ser Arg Thr Pro Glu Val Thr Cys Val Val Val Asp<br>270                    275                    280 | 2279 |
| gtg agc cac gaa gac cct gag gtc aag ttc aac tgg tac gtg<br>Val Ser His Glu Asp Pro Glu Val Lys Phe Asn Trp Tyr Val<br>          285                    290                    295 | 2321 |
| gac ggc gtg gag gtg cat aac gcc aag aca aag ccg cgg gag<br>Asp Gly Val Glu Val His Asn Ala Lys Thr Lys Pro Arg Glu<br>                    300                    305                    310 | 2363 |
| gag cag tac aac agc acg tac cgg gtg gtc agc gtc ctc acc<br>Glu Gln Tyr Asn Ser Thr Tyr Arg Val Val Ser Val Leu Thr<br>                        315                    320                    325 | 2405 |
| gtc ctg cac cag gac tgg ctg aat ggc aag gag tac aag tgc<br>Val Leu His Gln Asp Trp Leu Asn Gly Lys Glu Tyr Lys Cys<br>                                330                    335 | 2447 |
| aag gtc tcc aac aaa gcc ctc cca gcc ccc atc gag aaa acc<br>Lys Val Ser Asn Lys Ala Leu Pro Ala Pro Ile Glu Lys Thr<br>340                    345                    350 | 2489 |
| atc tcc aaa gcc aaa ggg cag ccc cga gaa cca cag gtg tac<br>Ile Ser Lys Ala Lys Gly Gln Pro Arg Glu Pro Gln Val Tyr<br>          355                    360                    365 | 2531 |
| acc ctg ccc cca tcc cgg gag gag atg acc aag aac cag gtc<br>Thr Leu Pro Pro Ser Arg Glu Glu Met Thr Lys Asn Gln Val<br>                    370                    375                    380 | 2573 |
| agc ctg acc tgc ctg gtc aaa ggc ttc tat ccc agc gac atc | 2615 |

```
                Ser Leu Thr Cys Leu Val Lys Gly Phe Tyr Pro Ser Asn Ile
                            385                 390                 395 gcc gtg gag tgg gag agc aat ggg cag ccg gag aac aac tac            2657
Ala Val Glu Trp Glu Ser Asn Gly Gln Pro Glu Asn Asn Tyr
                400                 405 aag acc acg cct ccc gtg ctg gac tcc gac ggc tcc ttc ttc            2699
Lys Thr Thr Pro Pro Val Leu Asp Ser Asp Gly Ser Phe Phe
410                 415                 420 ctc tac agc aag ctc acc gtg gac aag agc agg tgg cag cag            2741
Leu Tyr Ser Lys Leu Thr Val Asp Lys Ser Arg Trp Gln Gln
        425                 430                 435 ggg aac gtc ttc tca tgc tcc gtg atg cat gag gct ctg cac            2783
Gly Asn Val Phe Ser Cys Ser Val Met His Glu Ala Leu His
                440                 445                 450 aac cac tac acg cag aag agc ctc tcc ctg tct ccg ggt aaa            2825
Asn His Tyr Thr Gln Lys Ser Leu Ser Leu Ser Pro Gly Lys
                    455                 460                 465 tga gctagaaact aactaagcta gcaacggttt ccctctagcg ggatcaattc         2878 cgccccccc ccctaacgtt actggccgaa gccgcttgga ataaggccgg              2928
tgtgcgtttg tctatatgtt attttccacc atattgccgt cttttggcaa             2978
tgtgagggcc cggaaacctg gccctgtctt cttgacgagc attcctaggg             3028
gtctttcccc tctcgccaaa ggaatgcaag gtctgttgaa tgtcgtgaag             3078
gaagcagttc ctctggaagc ttcttgaaga caaacaacgt ctgtagcgac             3128
cctttgcagg cagcggaacc ccccacctgg cgacaggtgc ctctgcggcc             3178
aaaagccacg tgtataagat acacctgcaa aggcggcaca accccagtgc             3228
cacgttgtga gttggatagt tgtggaaaga gtcaaatggc tctcctcaag             3278
cgtattcaac aaggggctga aggatgccca gaaggtaccc cattgtatgg             3328
gatctgatct ggggcctcgg tgcacatgct ttacgtgtgt ttagtcgagg             3378
ttaaaaaacg tctaggcccc ccgaaccacg ggacgtggt tttcctttga              3428 aaaacacgat aataccatgg ttcgaccatt gaactgcatc gtcgccgtgt             3478
cccaaaatat ggggattggc aagaacggag acctaccctg gcctccgctc             3528
aggaacgagt tcaagtactt ccaaagaatg accacaacct cttcagtgga             3578
aggtaaacag aatctggtga ttatgggtag gaaaacctgg ttctccattc             3628
ctgagaagaa tcgacctttg aaggacagaa ttaatggttc gatatagttc             3678
tcagtagaga actcaaagaa ccaccacgag gagctcattt tcttgccaaa             3728
agtttggatg atgcccttaag acttattgaa caaccggaat tggcaagtaa            3778
agtagacatg gtttggatag tcggaggcag ttctgtttac caggaagcca             3828
tgaatcaacc aggccacctc agactctttg tgacaaggat catgcaggaa             3878
tttgaaagtg acacgttttt cccagaaatt gatttgggga aatataaact              3928
tctcccagaa tacccaggcg tcctctctga ggtccaggag gaaaaaggca             3978
tcaagtataa gtttgaagtc tacgagaaga aagactaaca ggaagatgct             4028
ttcaagttct ctgctcccct cctaaagcta tgcatttta taagaccatg              4078 ggacttttgc tggtcgatcg acctggcgta atagcgaaga ggcccgcacc             4128
gatcgccctt cccaacagtt gcgcagcctg aatggcgaat gggacgcgcc             4178
ctgtagcggc gcattaagcg cggcgggtgt ggtggttacg cgcagcgtga             4228
```

| | |
|---|---|
| ccgctacact tgccagcgcc ctagcgcccg ctcctttcgc tttcttccct | 4278 |
| tcctttctcg ccacgttcgc cggctttccc cgtcaagctc taaatcgggg | 4328 |
| gctcccttta gggttccgat ttagtgcttt acggcacctc gaccccaaaa | 4378 |
| aacttgatta gggtgatggt tcacgtagtg ggccatcgcc ctgatagacg | 4428 |
| gtttttcgcc tttgacgttg gagtccacgt tctttaatag tggactcttg | 4478 |
| ttccaaactg gaacaacact caaccctatc tcggtctatt tataagggat | 4528 |
| tttgccgatt tcggcctatt ggttaaaaaa tgagctgatt taacaaaatt | 4578 |
| taacgcgaat tttaacaaaa tattaacgct tacaatttag gtggcacttt | 4628 |
| tcggggaaat gtgcgcggaa cccctatatt tgtttatttt tctaaataca | 4678 |
| ttcaaatatg tatccgctca tgagacaata accctgataa atgcttcaat | 4728 |
| aatattgaaa aaggaagagt atgagtattc aacatttccg tgtcgccctt | 4778 |
| attccctttt ttgcggcatt ttgccttact gttttttgctc acccagaaac | 4828 |
| gctggtgaaa gtaaaagatg ctgaagatca gttgggtgca cgagtgggtt | 4878 |
| acatcgaact ggatctcaac agcggtaaga tccttgagag ttttcgcccc | 4928 |
| gaagaacgtt ttccaatgat gagcactttt aaagttctgc tatgtggcgc | 4978 |
| ggtattatcc cgtattgacg ccgggcaaga gcaactcggt cgccgcatac | 5028 |
| actattctca gaatgacttg gttgagtact caccagtcac agaaaagcat | 5078 |
| attacggatg gcatgacagt aagagaatta tgcagtgctg ccataaccat | 5128 |
| gagtgataac actgcggcca acttacttct gacaacgatc ggaggaccga | 5178 |
| aggagctaac cgcttttttg cacaacatgg gggatcatgt aactcgcctt | 5228 |
| gatcgttggg aaccggagct gaatgaagcc ataccaaacg acgagcgtga | 5278 |
| caccacgatg cctgtagcaa tggcaacaac gttgcgcaaa ctattaactg | 5328 |
| gcgaactact tactctagct tcccggcaac aattaataga ctggatggag | 5378 |
| gcggataaag ttgcaggacc acttctgcgc tcggcccttc cggctggctg | 5428 |
| gtttattgct gataaatctg gagccggtga gcgtgggtct cgcggtatca | 5478 |
| ttgcagcact ggggccagat ggtaagccct cccgtatcgt agttatctac | 5528 |
| acgacgggga gtcaggcaac tatggatgaa cgaaatagac agatcgctga | 5578 |
| gataggtgcc tcactgatta agcattggta actgtcagac caagtttact | 5628 |
| catatatact ttagattgat ttaaaacttc attttttaatt taaaaggatc | 5678 |
| taggtgaaga tccttttttga taatctcatg accaaaatcc cttaacgtga | 5728 |
| gttttcgttc cactgagcgt cagacccccgt agaaaagatc aaaggatctt | 5778 |
| cttgagatcc ttttttttctg cacgtaaatct gctgcttgca acaaaaaaac | 5828 |
| caccgctacc agcggtggtt tgtttgccgg atcaagagct accaactctt | 5878 |
| tttccgaagg taactggctt cagcagagcg cagataccaa atactgtcct | 5928 |
| tctagtgtag ccgtagttag gccaccactt caagaactct gtagcaccgc | 5978 |
| ctacatacct cgctctgcta atcctgttac cagtggctgc tgccagtggc | 6028 |
| gataagtcgt gtcttaccgg gttggactca agacgatagt taccggataa | 6078 |
| ggcgcagcgg tcgggctgaa cggggggttc gtgcacacag cccagcttgg | 6128 |
| agcgaacgac ctacaccgaa ctgagatacc tacagcgtga gctatgagaa | 6178 |
| agcgccacgc ttcccgaagg gagaaaggcg gacaggtatc cggtaagcgg | 6228 |

```
cagggtcgga acaggagagc gcacgaggga gcttccaggg ggaaacgcct         6278
ggtatcttta tagtcctgtc gggtttcgcc acctctgact tgagcgtcga         6328
tttttgtgat gctcgtcagg ggggcggagc ctatggaaaa acgccagcaa         6378
cgcggccttt ttacggttcc tggccttttg ctggccttttt gctcacatgt        6428 tctttcctgc gttatcccct gattctgtgg ataaccgtat taccgccttt         6478
gagtgagctg ataccgctcg ccgcagccga acgaccgagc gcagcgagtc         6528
agtgagcgag gaagcggaag agcgcccaat acgcaaaccg cctctccccg         6578
cgcgttggcc gattcattaa tgcaggtatc acgaggccct ttcgtcttca c        6629
```

<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37
ttcttgaagt ctggtgatgc tgcc         24

<210> SEQ ID NO 38
<211> LENGTH: 31
<212> TYPE: DNA
<213> ORGANISM: Artificial Sequence
<220> FEATURE:
<223> OTHER INFORMATION: primer

<400> SEQUENCE: 38
caagctagcc ctctaagact cctcccctgt t         31

<210> SEQ ID NO 39
<211> LENGTH: 33
<212> TYPE: DNA
<213> ORGANISM: Artificial Sequence
<220> FEATURE:
<223> OTHER INFORMATION: primer

<400> SEQUENCE: 39
gaactcgagt catttacccg gagacaggga gag         33

<210> SEQ ID NO 40
<211> LENGTH: 32
<212> TYPE: DNA
<213> ORGANISM: Artificial Sequence
<220> FEATURE:
<223> OTHER INFORMATION: primer

<400> SEQUENCE: 40
gcgccatggc ccaggtgcaa ctgcagcagt ca         32

<210> SEQ ID NO 41
<211> LENGTH: 34
<212> TYPE: DNA
<213> ORGANISM: Artificial Sequence
<220> FEATURE:
<223> OTHER INFORMATION: primer

<400> SEQUENCE: 41
cagggatcca ctcacctgag gagacggtga ccgt         34

<210> SEQ ID NO 42

```
<211> LENGTH: 33
<212> TYPE: DNA
<213> ORGANISM: Artificial Sequence
<220> FEATURE:
<223> OTHER INFORMATION: primer

<400> SEQUENCE: 42
agcgccatgg acatcgagct cactcagtct cca                                33

<210> SEQ ID NO 43
<211> LENGTH: 35
<212> TYPE: DNA
<213> ORGANISM: Artificial Sequence
<220> FEATURE:
<223> OTHER INFORMATION: primer

<400> SEQUENCE: 43
cagggatcca actcacgttt gatttccagc ttggt                              35

<210> SEQ ID NO 44
<211> LENGTH: 465
<212> TYPE: DNA
<213> ORGANISM: Mus Musculus
<220> FEATURE:
<223> OTHER INFORMATION: nucleotide sequence of murine heavy chain
      variable region

<400> SEQUENCE: 44
gtttaaacgc cgccaccatg aactggacct ggaccgtgtt ttgcctgctc               50
gctgtggctc ctggggccca cagcgccatg gcccaggtgc aactgcagca              100
gtcaggggct gagctggcta gacctggggc ttcagtgaag atgtcctgca              150
aggcttctgg ctacaccttt actacctaca atatacactg ggtaagacag              200
aggcctggac acgatctgga atggattgga tacattaatc ctagcagtgg              250
atattctgac tacaatcaaa gcttcaaggg caagaccaca ttgactgcag              300
acaagtcctc caacacagcc tacatgcaac tgaacagcct gacatctgag              350
gactctgcgg tctattactg tgcaagaaga gcggactatg taactacga               400 atatacctgg tttgcttact ggggccaagg gaccacggtc accgtctcct              450
caggtgagtg gatcc                                                    465

<210> SEQ ID NO 45
<211> LENGTH: 145
<212> TYPE: PRT
<213> ORGANISM: Mus musculus
<220> FEATURE:
<223> OTHER INFORMATION: amino acid sequence for murine heavy chain
      variable region

<400> SEQUENCE: 45

Met Asn Trp Thr Trp Thr Val Phe Cys Leu Leu Ala Val Ala Pro Gly
                 5                  10                  15

Ala His Ser Ala Met Ala Gln Val Gln Leu Gln Gln Ser Gly Ala Glu
            20                  25                  30

Leu Ala Arg Pro Gly Ala Ser Val Lys Met Ser Cys Lys Ala Ser Gly
        35                  40                  45

Tyr Thr Phe Thr Thr Tyr Thr Ile His Trp Val Arg Gln Arg Pro Gly
     50                  55                  60

His Asp Leu Glu Trp Ile Gly Tyr Ile Asn Pro Ser Ser Gly Tyr Ser
65                   70                  75                  80
```

```
Asp Tyr Asn Gln Ser Phe Lys Gly Lys Thr Thr Leu Thr Ala Asp Lys
            85                  90                  95
Ser Ser Asn Thr Ala Tyr Met Gln Leu Asn Ser Leu Thr Ser Glu Asp
            100                 105                 110
Ser Ala Val Tyr Tyr Cys Ala Arg Arg Ala Asp Tyr Gly Asn Tyr Glu
            115                 120                 125
Tyr Thr Trp Phe Ala Tyr Trp Gly Gln Gly Thr Thr Val Thr Val Ser
    130                 135                 140
Ser
145

<210> SEQ ID NO 46
<211> LENGTH: 415
<212> TYPE: DNA
<213> ORGANISM: Mus musculus
<220> FEATURE:
<223> OTHER INFORMATION: nucleotide sequence for murine light chain
      variable region

<400> SEQUENCE: 46
gtttaaacgc cgccaccatg aactggacct ggaccgtgtt ttgcctgctc         50
gctgtggctc ctggggccca cagcgccatg gacatcgagc tcactcagtc        100
tccaaaattc atgtccacat cagtaggaga cagggtcaac gtcacctaca        150
aggccagtca gaatgtgggt actaatgtag cctggtttca acaaaaacca        200
gggcaatctc ctaaagttct gatttactcg gcatcttacc gatacagtgg        250
agtccctgat cgcttcacag gcagtggatc tggaacagat ttcactctca        300
ccatcagcaa tgtgcagtct gaagacttgg cagagtattt ctgtcagcaa        350
tatcacacct atcctctcac gttcggaggg ggcaccaagc tggaaatcaa        400
acgtgagttg gatcc                                              415

<210> SEQ ID NO 47
<211> LENGTH: 129
<212> TYPE: PRT
<213> ORGANISM: Mus musculus
<220> FEATURE:
<223> OTHER INFORMATION: amino acid sequence for murine light chain
      variable region

<400> SEQUENCE: 47

Met Asn Trp Thr Trp Thr Val Phe Cys Leu Leu Ala Val Ala Pro Gly
                5                   10                  15
Ala His Ser Ala Met Asp Ile Glu Leu Thr Gln Ser Pro Lys Phe Met
            20                  25                  30
Ser Thr Ser Val Gly Asp Arg Val Asn Val Thr Tyr Lys Ala Ser Gln
        35                  40                  45
Asn Val Gly Thr Asn Val Ala Trp Phe Gln Gln Lys Pro Gly Gln Ser
    50                  55                  60
Pro Lys Val Leu Ile Tyr Ser Ala Ser Tyr Arg Tyr Ser Gly Val Pro
65                  70                  75                  80
Asp Arg Phe Thr Gly Ser Gly Ser Gly Thr Asp Phe Thr Leu Thr Ile
                85                  90                  95
Ser Asn Val Gln Ser Glu Asp Leu Ala Glu Tyr Phe Cys Gln Gln Tyr
            100                 105                 110
His Thr Tyr Pro Leu Thr Phe Gly Gly Gly Thr Lys Leu Glu Ile Lys
        115                 120                 125
```

Arg

<210> SEQ ID NO 48
<211> LENGTH: 5759
<212> TYPE: DNA
<213> ORGANISM: Artificial Sequence
<220> FEATURE:
<223> OTHER INFORMATION: Light chain expression vector pREN-Neo which is
      a mammalian cell expression vector used to produce chimeric
      and reshaped human antibodies with human kappa light chains and
      human gamma-1 heav
<400> SEQUENCE: 48

| | |
|---|---:|
| ctcgagagcg ggcagtgagc gcaacgcaat taatgtgagt tagctcactc | 50 |
| attaggcacc ccaggcttta cactttatgc tcccggctcg tatgttgtgt | 100 |
| ggagattgtg agcggataac aatttcacac agaattcgtg aggctccggt | 150 |
| gcccgtcagt gggcagagcg cacatcgccc acagtccccg agaagttggg | 200 |
| gggaggggtc ggcaattgaa ccggtgccta gagaaggtgg cgcggggtaa | 250 |
| actgggaaag tgatgtcgtg tactggctcc gcctttttcc cgagggtggg | 300 |
| ggagaaccgt ataaagtgc agtagtcgcc gtgaacgttc ttttcgcaa | 350 |
| cgggtttgcc gccagaacac aggtaagtgc cgtgtgtggt tcccgcgggc | 400 |
| ctggcctctt tacgggttat ggcccttgcg tgccttgaat tacttccacg | 450 |
| cccctggctg cagtacgtga ttcttgatcc cgagcttcgg gttggaagtg | 500 |
| ggtgggagag ttcgaggcct tgcgcttaag gagccccttc gcctcgtgct | 550 |
| tgagttgagg cctggcctgg gcgctgggc cgccgcgtgc gaatctggtg | 600 |
| gcaccttcgc gcctgtctcg ctgctttcga taagtctcta gccatttaaa | 650 |
| atttttgatg acctgctgcg acgctttttt tctggcaaga tagtcttgta | 700 |
| aatgcgggcc aagatctgca cactggtatt tcggttttg gggccgcggg | 750 |
| cggcgacggg gcccgtgcgt cccagcgcac atgttcggcg aggcggggcc | 800 |
| tgcgagcgcg gccaccgaga tcggacggg ggtagtctca agctggccgg | 850 |
| cctgctctgg tgcctggcct cgcgccgccg tgtatcgccc cgccctgggc | 900 |
| ggcaaggctg gcccggtcgg caccagttgc gtgagcggaa agatggccgc | 950 |
| ttccggcc tgctgcaggg agctcaaaat ggaggacgcg gcgctcggga | 1000 |
| gagcgggcgg gtgagtcacc cacacaaagg aaaagggcct ttccgtcctc | 1050 |
| agccgtcgct tcatgtgact ccacggagta ccgggcgccc tccaggcacc | 1100 |
| tcgattagtt ctcgagcttt tggagtacgt cgtctttagg ttgggggag | 1150 |
| gggttttatg cgatggagtt tccccacact gagtgggtgg agactgaagt | 1200 |
| taggccagct tggcacttga tgtaattctc cttggaattt gccctttttg | 1250 |
| agtttggatc ttggttcatt ctcaagcctc agacagtggt tcaaagtttt | 1300 |
| tttcttccat ttcaggtgta cgcgtctcgg gaagctttag tttaaacgcc | 1350 |
| gtgagtggat ccatctggga taagcatgct gttttctgtc tgtccctaac | 1400 |
| atgccctgtg attatgcgca aacaacacac ccaagggcag aactttgtta | 1450 |
| cttaaacacc atcctgtttg cttctttcct cagga act gtg gct gca cca | 1500 |
|                   Thr Val Ala Ala Pro | |
|                               5 | |
| tct gtc ttc atc ttc ccg cca tct gat gag cag ttg aaa tct gga | 1545 |
| Ser Val Phe Ile Phe Pro Pro Ser Asp Glu Gln Leu Lys Ser Gly | |
|   10          15          20 | |

| | |
|---|---|
| act gcc tct gtt gtg tgc ctg ctg aat aac ttc tat ccc aga gag<br>Thr Ala Ser Val Val Cys Leu Leu Asn Asn Phe Tyr Pro Arg Glu<br>                     25                      30                      35 | 1590 |
| gcc aaa gta cag tgg aag gtg gat aac gcc ctc caa tcg ggt aac<br>Ala Lys Val Gln Trp Lys Val Asp Asn Ala Leu Gln Ser Gly Asn<br>                     40                      45                      50 | 1635 |
| tcc cag gag agt gtc aca gag cag gac agc aag gac agc acc tac<br>Ser Gln Glu Ser Val Thr Glu Gln Asp Ser Lys Asp Ser Thr Tyr<br>                     55                      60                      65 | 1680 |
| agc ctc agc agc acc ctg acg ctg agc aaa gca gac tac gag aaa<br>Ser Leu Ser Ser Thr Leu Thr Leu Ser Lys Ala Asp Tyr Glu Lys<br>                     70                      75                      80 | 1725 |
| cac aaa gtc tac gcc tgc gaa gtc acc cat cag ggc ctg agc tcg<br>His Lys Val Tyr Ala Cys Glu Val Thr His Gln Gly Leu Ser Ser<br>                     85                      90                      95 | 1770 |
| ccc gtc aca aag agc ttc aac agg gga gag tgt tga<br>Pro Val Thr Lys Ser Phe Asn Arg Gly Glu Cys<br>                    100                     105 | 1806 |
| gctagaacta actaactaag ctagcaacgg tttccctcta gcgggatcaa | 1856 |
| ttccgccccc cccccctaac gttactggcc gaagccgctt ggaataaggc | 1906 |
| cggtgtgcgt ttgtctatat gttatttttcc accatattgc cgtcttttgg | 1956 |
| caatgtgagg gcccggaaac ctggccctgt cttcttgacg agcattccta | 2006 |
| ggggtctttc ccctctcgcc aaaggaatgc aaggtctgtt gaatgtcgtg | 2056 |
| aaggaagcag ttcctctgga agcttcttga agacaaacaa cgtctgtagc | 2106 |
| gaccctttgc aggcagcgga accccccacc tggcgacagg tgcctctgcg | 2156 |
| gccaaaagcc acgtgtataa gatacacctg caaaggcggc acaaccccag | 2206 |
| tgccacgttg tgagttggat agttgtggaa agagtcaaat ggctctcctc | 2256 |
| aagcgtattc aacaagggc tgaaggatgc cagaaggta ccccattgta | 2306 |
| tgggatctga tctggggcct cggtgcacat gctttacgtg tgtttagtcg | 2356 |
| aggttaaaaa acgtctaggc cccccgaacc acggggacgt ggttttcctt | 2406 |
| tgaaaaacac gataatacca tggttgaaca agatggattg cacgcaggtt | 2456 |
| ctccggccgc ttgggtggag aggctattcg gctatgactg ggcacaacag | 2506 |
| acaatcggct gctctgatgc cgccgtgttc cggctgtcag cgcaggggcg | 2556 |
| cccggttctt tttgtcaaga ccgacctgtc cggtgccctg aatgaactgc | 2606 |
| aggacgaggc agcgcggcta tcgtggctgg ccacgacggg cgttccttgc | 2656 |
| gcagctgtgc tcgacgttgt cactgaagcg ggaagggact ggctgctatt | 2706 |
| gggcgaagtg ccggggcagg atctcctgtc atctcacctt gctcctgccg | 2756 |
| agaaagtatc catcatggct gatgcaatgc ggcggctgca tacgcttgat | 2806 |
| ccggctacct gcccattcga ccaccaagcg aaacatcgca tcgagcgagc | 2856 |
| acgtactcgg atggaagccg gtcttgtcga tcaggatgat ctggacgaag | 2906 |
| agcatcaggg gctcgcgcca gccgaactgt tcgccaggct caaggcgcgc | 2956 |
| atgcccgacg gcgaggatct cgtcgtgacc catggcgatg cctgcttgcc | 3006 |
| gaatatcatg gtggaaaatg gccgcttttc tggattcatc gactgtggcc | 3056 |
| ggctgggtgt ggcggaccgc tatcaggaca tagcgttggc tacccgtgat | 3106 |
| attgctgaag agcttggcgg cgaatgggct gaccgcttcc tcgtgcttta | 3156 |

-continued

```
cggtatcgcc gctcccgatt cgcagcgcat cgccttctat cgccttcttg    3206
acgagttctt ctgagtcgat cgacctggcg taatagcgaa gaggcccgca    3256
ccgatcgccc ttcccaacag ttgcgcagcc tgaatggcga atgggacgcg    3306
ccctgtagcg gcgcattaag cgcggcgggt gtggtggtta cgcgcagcgt    3356
gaccgctaca cttgccagcg ccctagcgcc cgctcctttc gctttcttcc    3406
cttcctttct cgccacgttc gccggctttc cccgtcaagc tctaaatcgg    3456
gggctccctt tagggttccg atttagtgct ttacggcacc tcgaccccaa    3506
aaaacttgat tagggtgatg gttcacgtag tgggccatcg ccctgataga    3556
cggttttttcg cctttgacgt tggagtccac gttctttaat agtggactct    3606
tgttccaaac tggaacaaca ctcaacccta tctcggtcta tttataaggg    3656
attttgccga tttcggccta ttggttaaaa atgagctga tttaacaaaa    3706
tttaacgcga attttaacaa aatattaacg cttacaattt aggtggcact    3756
tttcggggaa atgtgcgcgg aacccctata tttgtttatt tttctaaata    3806
cattcaaata tgtatccgct catgagacaa taaccctgat aaatgcttca    3856
ataatattga aaaaggaaga gtatgagtat tcaacatttc cgtgtcgccc    3906
ttattccctt ttttgcggca ttttgcctta ctgttttttgc tcacccagaa    3956
acgctggtga agtaaaaga tgctgaagat cagttgggtg cacgagtggg    4006
ttacatcgaa ctggatctca acagcggtaa gatccttgag agttttcgcc    4056
ccgaagaacg ttttccaatg atgagcactt ttaaagttct gctatgtggc    4106
gcggtattat cccgtattga cgccgggcaa gagcaactcg gtcgccgcat    4156
acactattct cagaatgact tggttgagta ctcaccagtc acagaaaagc    4206
atattacgga tggcatgaca gtaagagaat tatgcagtgc tgccataacc    4256
atgagtgata acactgcggc caacttactt ctgacaacga tcggaggacc    4306
gaaggagcta accgcttttt tgcacaacat ggggatcat gtaactcgcc    4356
ttgatcgttg ggaaccggag ctgaatgaag ccataccaaa cgacgagcgt    4406
gacaccacga tgcctgtagc aatggcaaca acgttgcgca aactattaac    4456
tggcgaacta cttactctag cttcccggca acaattaata gactggatgg    4506
aggcggataa agttgcagga ccacttctgc gctcggccct tccggctggc    4556
tggtttattg ctgataaatc tggagccggt gagcgtgggt ctcgcggtat    4606
cattgcagca ctggggccag atggtaagcc ctcccgtatc gtagttatct    4656
acacgacggg gagtcaggca actatggatg aacgaaatag acagatcgct    4706
gagataggtg cctcactgat taagcattgg taactgtcag accaagttta    4756
ctcatatata ctttagattg atttaaaact tcatttttaa tttaaaagga    4806
tctaggtgaa gatcctttt gataatctca tgaccaaaat cccttaacgt    4856
gagttttcgt tccactgagc gtcagacccc gtagaaaaga tcaaaggatg    4906
ttcttgagat cctttttttc tgcacgtaat ctgctgcttg caaacaaaaa    4956
accaccgcta ccagcggtgg tttgtttgcc ggatcaagag ctaccaactc    5006
ttttccgaa ggtaactggc ttcagcagag cgcagatacc aaatactgtc    5056
cttctagtgt agccgtagtt aggccaccac ttcaagaact ctgtagcacc    5106
gcctacatac ctcgctctgc taatcctgtt accagtggct gctgccagtg    5156
```

-continued

| | |
|---|---|
| gcgataagtc gtgtcttacc gggttggact caagacgata gttaccggat | 5206 |
| aaggcgcagc ggtcgggctg aacggggggt tcgtgcacac agcccagctt | 5256 |
| ggagcgaacg acctacaccg aactgagata cctacagcgt gagctatgag | 5306 |
| aaagcgccac gcttcccgaa gggagaaagg cggacaggta tccggtaagc | 5356 |
| ggcagggtcg aacaggaga gcgcacgagg gagcttccag ggggaaacgc | 5406 |
| ctggtatctt tatagtcctg tcgggtttcg ccacctctga cttgagcgtc | 5456 |
| gatttttgtg atgctcgtca ggggggcgga gcctatggaa aaacgccagc | 5506 |
| aacgcggcct ttttacggtt cctggccttt tgctggcctt ttgctcacat | 5556 |
| gttctttcct gcgttatccc ctgattctgt ggataaccgt attaccgcct | 5606 |
| ttgagtgagc tgataccgct cgccgcagcc gaacgaccga gcgcagcgag | 5656 |
| tcagtgagcg aggaagcgga agagcgccca atacgcaaac cgcctctccc | 5706 |
| cgcgcgttgg ccgattcatt aatgcaggta tcacgaggcc ctttcgtctt cac | 5759 |

<210> SEQ ID NO 49
<211> LENGTH: 6207
<212> TYPE: DNA
<213> ORGANISM: Artificial Sequence
<220> FEATURE:
<223> OTHER INFORMATION: Heavy chain expression vector pREN-DHFR which
    is a mammalian cell expression vector used to produce chimeric and
    reshaped human antibodies with human kappa light chains and human
    gamma-1 hea
<400> SEQUENCE: 49

| | |
|---|---|
| ctcgagagcg ggcagtgagc gcaacgcaat taatgtgagt tagctcactc | 50 |
| attaggcacc ccaggcttta cactttatgc tcccggctcg tatgttgtgt | 100 |
| ggagattgtg agcggataac aatttcacac agaattcgtg aggctccggt | 150 |
| gcccgtcagt gggcagagcg cacatcgccc acagtccccg agaagttggg | 200 |
| gggaggggtc ggcaattgaa ccggtgccta gagaaggtgg cgcggggtaa | 250 |
| actgggaaag tgatgtcgtg tactggctcc gcctttttcc cgagggtggg | 300 |
| ggagaaccgt atataagtgc agtagtcgcc gtgaacgttc tttttcgcaa | 350 |
| cgggtttgcc gccagaacac aggtaagtgc cgtgtgtggt tcccgcgggc | 400 |
| ctggcctctt tacgggttat ggcccttgcg tgccttgaat tacttccacg | 450 |
| cccctggctg cagtacgtga ttcttgatcc cgagcttcgg gttggaagtg | 500 |
| ggtgggagag ttcgaggcct tgcgcttaag agcccccttc gcctcgtgct | 550 |
| tgagttgagg cctggcctgg gcgctgggc cgccgcgtgc gaatctggtg | 600 |
| gcaccttcgc gcctgtctcg ctgctttcga taagtctcta gccatttaaa | 650 |
| attttgatg acctgctgcg acgctttttt tctggcaaga tagtcttgta | 700 |
| aatgcgggcc aagatctgca cactggtatt tcggttttg gggccgcggg | 750 |
| cggcgacggg gcccgtgcgt cccagcgcac atgttcggcg aggcggggcc | 800 |
| tgcgagcgcg gccaccgaga tcggacgggg ggtagtctca agctggccgg | 850 |
| cctgctctgg tgcctggcct cgcgccgccg tgtatcgccc cgccctgggc | 900 |
| ggcaaggctg gcccggtcgg caccagttgc gtgagcggaa agatggccgc | 950 |
| ttcccgccc tgctgcaggg agctcaaaat ggaggacgcg gcgctcggga | 1000 |
| gagcgggcgg gtgagtcacc cacacaaagg aaaagggcct ttccgtcctc | 1050 |

-continued

```
agccgtcgct tcatgtgact ccacggagta ccgggcgccg tccaggcacc           1100
tcgattagtt ctcgagcttt tggagtacgt cgtctttagg ttgggggag            1150 gggttttatg cgatggagtt tccccacact gagtgggtgg agactgaagt           1200
taggccagct tggcacttga tgtaattctc cttggaattt gcccttttg            1250 agtttggatc ttggttcatt ctcaagcctc agacagtggt tcaaagtttt           1300
cttccatttc aggtgtacgc gtctcgggaa gctttagttt aaacgcctgg           1350
atcctctgcg cctgggccca gctctgtccc acaccgcggt cacatggcac           1400
cacctctctt gcagcc tcc acc aag ggc cca tcg gtc ttc ccc ctg        1446
              Ser Thr Lys Gly Pro Ser Val Phe Pro Leu
                              5                  10 gca ccc tcc tcc aag agc acc tct ggg ggc aca gcg gcc ctg ggc      1491
Ala Pro Ser Ser Lys Ser Thr Ser Gly Gly Thr Ala Ala Leu Gly
                15                  20                  25 tgc ctg gtc aag gac tac ttc ccc gaa ccg gtg acg gtg tcg tgg      1536
Cys Leu Val Lys Asp Tyr Phe Pro Glu Pro Val Thr Val Ser Trp
                30                  35                  40 aac tca ggc gcc ctg acc agc ggc gtg cac acc ttc ccg gct gtc      1581
Asn Ser Gly Ala Leu Thr Ser Gly Val His Thr Phe Pro Ala Val
                45                  50                  55 cta cag tcc tca gga ctc tac tcc ctc agc agc gtg gtg acc gtg      1626
Leu Gln Ser Ser Gly Leu Tyr Ser Leu Ser Ser Val Val Thr Val
                60                  65                  70 ccc tcc agc agc ttg ggc acc cag acc tac atc tgc aac gtg aat      1671
Pro Ser Ser Ser Leu Gly Thr Gln Thr Tyr Ile Cys Asn Val Asn
                75                  80                  85 cac aag ccc agc aac acc aag gtg gac aag aaa gtt gag ccc aaa      1716
His Lys Pro Ser Asn Thr Lys Val Asp Lys Lys Val Glu Pro Lys
                90                  95                 100 tct tgt gac aaa act cac aca tgc cca ccg tgc cca gca cct gaa      1761
Ser Cys Asp Lys Thr His Thr Cys Pro Pro Cys Pro Ala Pro Glu
               105                 110                 115 ctc ctg ggg gga ccg tca gtc ttc ctc ttc ccc cca aaa ccc aag      1806
Leu Leu Gly Gly Pro Ser Val Phe Leu Phe Pro Pro Lys Pro Lys
               120                 125                 130 gac acc ctc atg atc tcc cgg acc cct gag gtc aca tgc gtg gtg      1851
Asp Thr Leu Met Ile Ser Arg Thr Pro Glu Val Thr Cys Val Val
               135                 140                 145 gtg gac gtg agc cac gaa gac cct gag gtc aag ttc aac tgg tac      1896
Val Asp Val Ser His Glu Asp Pro Glu Val Lys Phe Asn Trp Tyr
               150                 155                 160 gtg gac ggc gtg gag gtg cat aac gcc aag aca aag ccg cgg gag      1941
Val Asp Gly Val Glu Val His Asn Ala Lys Thr Lys Pro Arg Glu
               165                 170                 175 gag cag tac aac agc acg tac cgg gtg gtc agc gtc ctc acc gtc      1986
Glu Gln Tyr Asn Ser Thr Tyr Arg Val Val Ser Val Leu Thr Val
               180                 185                 190 ctg cac cag gac tgg ctg aat ggc aag gag tac aag tgc aag gtc      2031
Leu His Gln Asp Trp Leu Asn Gly Lys Glu Tyr Lys Cys Lys Val
               195                 200                 205 tcc aac aaa gcc ctc cca gcc ccc atc gag aaa acc atc tcc aaa      2076
Ser Asn Lys Ala Leu Pro Ala Pro Ile Glu Lys Thr Ile Ser Lys
               210                 215                 220 gcc aaa ggg cag ccc cga gaa cca cag gtg tac acc ctg ccc cca      2121
Ala Lys Gly Gln Pro Arg Glu Pro Gln Val Tyr Thr Leu Pro Pro
               225                 230                 235 tcc cgg gag gag atg acc aag aac cag gtc agc ctg acc tgc ctg      2166
```

```
Ser Arg Glu Glu Met Thr Lys Asn Gln Val Ser Leu Thr Cys Leu
            240                 245                 250 gtc aaa ggc ttc tat ccc agc gac atc gcc gtg gag tgg gag agc       2211
Val Lys Gly Phe Tyr Pro Ser Asp Ile Ala Val Glu Trp Glu Ser
            255                 260                 265 aat ggg cag ccg gag aac aac tac aag acc acg cct ccc gtg ctg       2256
Asn Gly Gln Pro Glu Asn Asn Tyr Lys Thr Thr Pro Pro Val Leu
            270                 275                 280 gac tcc gac ggc tcc ttc ttc ctc tac agc aag ctc acc gtg gac       2301
Asp Ser Asp Gly Ser Phe Phe Leu Tyr Ser Lys Leu Thr Val Asp
            285                 290                 295 aag agc agg tgg cag cag ggg aac gtc ttc tca tgc tcc gtg atg       2346
Lys Ser Arg Trp Gln Gln Gly Asn Val Phe Ser Cys Ser Val Met
            300                 305                 310 cat gag gct ctg cac aac cac tac acg cag aag agc ctc tcc ctg       2391
His Glu Ala Leu His Asn His Tyr Thr Gln Lys Ser Leu Ser Leu
            315                 320                 325 tct ccg ggt aaa tga gctagaaact aactaagcta gcaacggttt              2436
Ser Pro Gly Lys ccctctagcg ggatcaattc cgcccccccc ccctaacgtt actggccgaa            2486
gccgcttgga ataaggccgg tgtgcgtttg tctatatgtt attttccacc            2536
atattgccgt cttttggcaa tgtgagggcc cggaaacctg gccctgtctt            2586
cttgacgagc attcctaggg gtctttcccc tctcgccaaa ggaatgcaag            2636
gtctgttgaa tgtcgtgaag gaagcagttc ctctggaagc ttcttgaaga            2686
caaacaacgt ctgtagcgac cctttgcagg cagcggaacc ccccacctgg            2736
cgacaggtgc ctctgcggcc aaaagccacg tgtataagat acacctgcaa            2786
aggcggcaca accccagtgc cacgttgtga gttggatagt tgtggaaaga            2836
gtcaaatggc tctcctcaag cgtattcaac aaggggctga aggatgccca            2886
gaaggtaccc cattgtatgg gatctgatct ggggcctcgg tgcacatgct            2936
ttacgtgtgt ttagtcgagg ttaaaaaacg tctaggcccc ccgaaccacg            2986
gggacgtggt tttcctttga aaaacacgat aataccatgg ttcgaccatt            3036
gaactgcatc gtcgccgtgt cccaaaatat ggggattggc aagaacggag            3086
acctaccctg gcctccgctc aggaacgagt tcaagtactt ccaaagaatg            3136
accacaacct cttcagtgga aggtaaacag aatctggtga ttatgggtag            3186
gaaaacctgg ttctccattc ctgagaagaa tcgacccttta aaggacagaa           3236 ttaatggttc gatatagttc tcagtagaga actcaaagaa ccaccacgag            3286
gagctcattt tcttgccaaa agtttggatg atgccttaag acttattgaa            3336
caaccggaat tggcaagtaa agtagacatg gtttggatag tcggaggcag            3386
ttctgtttac caggaagcca tgaatcaacc aggccacctc agactctttg            3436
tgacaaggat catgcaggaa tttgaaagtg acacgttttt cccagaaatt            3486
gatttgggga aatataaaact tctcccagaa tacccaggcg tcctctctga           3536
ggtccaggag gaaaaaggca tcaagtataa gtttgaagtc tacgagaaga            3586
aagactaaca ggaagatgct ttcaagttct ctgctcccct cctaaagcta            3636
tgcattttta taagaccatg ggactttttgc tggtcgatcg acctggcgta           3686
atagcgaaga ggcccgcacc gatcgccctt cccaacagtt gcgcagcctg            3736
aatggcgaat gggacgcgcc ctgtagcggc gcattaagcg cggcgggtgt            3786
```

```
ggtggttacg cgcagcgtga ccgctacact tgccagcgcc ctagcgcccg      3836
ctcctttcgc tttcttccct tccttttctcg ccacgttcgc cggctttccc      3886
cgtcaagctc taaatcgggg gctcccttta gggttccgat ttagtgcttt      3936
acggcacctc gaccccaaaa aacttgatta gggtgatggt tcacgtagtg      3986
ggccatcgcc ctgatagacg ttttttcgcc tttgacgttg gagtccacgt      4036
tctttaatag tggactcttg ttccaaactg gaacaacact caaccctatc      4086
tcggtctatt tataagggat tttgccgatt tcggcctatt ggttaaaaaa      4136
tgagctgatt taacaaaatt taacgcgaat tttaacaaaa tattaacgct      4186
tacaatttag gtggcacttt tcggggaaat gtgcgcggaa cccctatatt      4236
tgtttatttt tctaaataca ttcaaatatg tatccgctca tgagacaata      4286
accctgataa atgcttcaat aatattgaaa aaggaagagt atgagtattc      4336
aacatttccg tgtcgccctt attccctttt ttgcggcatt ttgccttact      4386
gttttttgctc acccagaaac gctggtgaaa gtaaaagatg ctgaagatca      4436
gttgggtgca cgagtgggtt acatcgaact ggatctcaac agcggtaaga      4486
tccttgagag ttttcgcccc gaagaacgtt ttccaatgat gagcacttttt     4536
aaagttctgc tatgtggcgc ggtattatcc cgtattgacg ccgggcaaga      4586
gcaactcggt cgccgcatac actattctca gaatgacttg gttgagtact      4636
caccagtcac agaaaagcat attacggatg gcatgacagt aagagaatta      4686
tgcagtgctg ccataaccat gagtgataac actgcggcca acttacttct      4736
gacaacgatc ggaggaccga aggagctaac cgcttttttg cacaacatgg      4786
gggatcatgt aactcgcctt gatcgttggg aaccggagct gaatgaagcc      4836
ataccaaacg acgagcgtga caccacgatg cctgtagcaa tggcaacaac      4886
gttgcgcaaa ctattaactg gcgaactact tactctagct tcccggcaac      4936
aattaataga ctggatggag gcggataaag ttgcaggacc acttctgcgc      4986
tcggcccttc cggctggctg gtttattgct gataaatctg gagccggtga      5036
gcgtgggtct cgcggtatca ttgcagcact ggggccagat ggtaagccct      5086
cccgtatcgt agttatctac acgacgggga gtcaggcaac tatggatgaa      5136
cgaaatagac agatcgctga gataggtgcc tcactgatta agcattggta      5186
actgtcagac caagtttact catatatact ttagattgat ttaaaacttc      5236
attttttaatt taaaaggatc taggtgaaga tcctttttga taatctcatg      5286
accaaaatcc cttaacgtga gttttcgttc cactgagcgt cagaccccgt      5336
agaaaagatc aaaggatgtt cttgagatcc ttttttttctg cacgtaatct      5386
gctgcttgca aacaaaaaac caccgctacc agcggtggtt tgtttgccgg      5436
atcaagagct accaactctt tttccgaagg taactggctt cagcagagcg      5486
cagataccaa atactgtcct tctagtgtag ccgtagttag gccaccactt      5536
caagaactct gtagcaccgc ctacatacct cgctctgcta atcctgttac      5586
cagtggctgc tgccagtggc gataagtcgt gtcttaccgg gttggactca      5636
agacgatagt taccggataa ggcgcagcgg tcgggctgaa cggggggttc      5686
gtgcacacag cccagcttgg agcgaacgac ctacaccgaa ctgagatacc      5736
```

```
tacagcgtga gctatgagaa agcgccacgc ttcccgaagg gagaaaggcg            5786
gacaggtatc cggtaagcgg cagggtcgga acaggagagc gcacgaggga            5836
gcttccaggg ggaaacgcct ggtatcttta tagtcctgtc gggtttcgcc            5886
acctctgact tgagcgtcga tttttgtgat gctcgtcagg ggggcggagc            5936
ctatggaaaa acgccagcaa cgcggccttt ttacggttcc tggccttttg            5986
ctggcctttt gctcacatgt tctttcctgc gttatcccct gattctgtgg            6036
ataaccgtat taccgccttt gagtgagctg ataccgctcg ccgcagccga            6086
acgaccgagc gcagcgagtc agtgagcgag gaagcggaag agcgcccaat            6136
acgcaaaccg cctctccccg cgcgttggcc gattcattaa tgcaggtatc            6186
acgaggccct ttcgtcttca c                                           6207
```

<210> SEQ ID NO 50
<211> LENGTH: 444
<212> TYPE: DNA
<213> ORGANISM: Mus musculus
<220> FEATURE:
<223> OTHER INFORMATION: murine G250 heavy chain variable region

<400> SEQUENCE: 50

```
gtttaaacgc cgccaccatg aacttcgggc tcagattgat tttccttgtc             50
ctggttttaa aaggtgtcct gtgtgacgtg aagctcgtgg agtctggggc            100
agccttagtg aagcttggag ggtccctgaa actctcctgt gcagcctctg            150
gattcacttt cagtaactat tacatgtctt gggttcgcca gactccagag            200
aagaggctgg agttggtcgc agccattaat agtgatggtg gtatcaccta            250
ctatctagac actgtgaagg gccgattcac catttcaaga gacaatgcca            300
agaacaccct gtacctgcaa atgagcagtc tgaagtctga ggacacagcc            350
ttgttttact gtgcaagaca ccgctcaggc tacttttcta tggactactg            400
gggtcaagga acctcagtca ccgtctcctc aggtgagtgg atcc                  444
```

<210> SEQ ID NO 51
<211> LENGTH: 140
<212> TYPE: PRT
<213> ORGANISM: Mus musculus
<220> FEATURE:
<223> OTHER INFORMATION: amino acid sequence for murine G250 heavy chain
      variable region
<400> SEQUENCE: 51

```
Met Asn Phe Gly Leu Arg Leu Ile Phe Leu Val Leu Val Leu Lys Gly
                 5                  10                  15

Val Leu Cys Asp Val Lys Leu Val Glu Ser Gly Ala Ala Leu Val Lys
             20                  25                  30

Leu Gly Gly Ser Leu Lys Leu Ser Cys Ala Ala Ser Gly Phe Thr Phe
         35                  40                  45

Ser Asn Tyr Tyr Met Ser Trp Val Arg Gln Thr Pro Glu Lys Arg Leu
     50                  55                  60

Glu Leu Val Ala Ala Ile Asn Ser Asp Gly Gly Ile Thr Tyr Tyr Leu
 65                  70                  75                  80

Asp Thr Val Lys Gly Arg Phe Thr Ile Ser Arg Asp Asn Ala Lys Asn
                 85                  90                  95

Thr Leu Tyr Leu Gln Met Ser Ser Leu Lys Ser Glu Asp Thr Ala Leu
            100                 105                 110
```

-continued

```
Phe Tyr Cys Ala Arg His Arg Ser Gly Tyr Phe Ser Met Asp Tyr Trp
        115                 120                 125

Gly Gln Gly Thr Ser Val Thr Val Ser Ser Gly Glu
    130                 135                 140
```

<210> SEQ ID NO 52
<211> LENGTH: 423
<212> TYPE: DNA
<213> ORGANISM: Mus musculus
<220> FEATURE:
<223> OTHER INFORMATION: murine G250 light chain variable region

<400> SEQUENCE: 52

```
gtttaaacgc cgccaccatg ggcttcaaga tggagtttca tactcaggtc           50
tttgtattcg tgtttctctg gttgtctggt gttgatggag acattgtgat          100
gacccagtct caaagattca tgtccacaac agtaggagac agggtcagca          150
tcacctgcaa ggccagtcag aatgtggttt ctgctgttgc ctggtatcaa          200
cagaaaccag gacaatctcc taaactactg atttactcag catccaatcg          250
gtacactgga gtccctgatc gcttcacagg cagtggatct gggacagatt          300
tcactctcac cattagcaat atgcagtctg aagacctggc tgattttttc          350
tgtcaacaat atagcaacta tccgtggacg ttcggtggag gcaccaagct          400
ggaaatcaaa cgtgagtgga tcc                                       423
```

<210> SEQ ID NO 53
<211> LENGTH: 132
<212> TYPE: PRT
<213> ORGANISM: Mus musculus
<220> FEATURE:
<223> OTHER INFORMATION: amino acid sequence for murine G250 light chain
      variable region
<400> SEQUENCE: 53

```
Met Gly Phe Lys Met Glu Phe His Thr Gln Val Phe Val Phe Val Phe
                5                  10                  15

Leu Trp Leu Ser Gly Val Asp Gly Asp Ile Val Met Thr Gln Ser Gln
            20                  25                  30

Arg Phe Met Ser Thr Thr Val Gly Asp Arg Val Ser Ile Thr Cys Lys
        35                  40                  45

Ala Ser Gln Asn Val Val Ser Ala Val Ala Trp Tyr Gln Gln Lys Pro
    50                  55                  60

Gly Gln Ser Pro Lys Leu Leu Ile Tyr Ser Ala Ser Asn Arg Tyr Thr
65                  70                  75                  80

Gly Val Pro Asp Arg Phe Thr Gly Ser Gly Ser Gly Thr Asp Phe Thr
                85                  90                  95

Leu Thr Ile Ser Asn Met Gln Ser Glu Asp Leu Ala Asp Phe Phe Cys
            100                 105                 110

Gln Gln Tyr Ser Asn Tyr Pro Trp Thr Phe Gly Gly Gly Thr Lys Leu
        115                 120                 125

Glu Ile Lys Arg
    130
```

<210> SEQ ID NO 54
<211> LENGTH: 482
<212> TYPE: DNA
<213> ORGANISM: Homo sapiens
<220> FEATURE:
<223> OTHER INFORMATION: nucleotide sequence of a TNF fragment -continued

<400> SEQUENCE: 54

```
ccatggtctc atcttctcga accccgagtg acaagcctgt agcccatgtt        50
gtagcaaacc ctcaagctga ggggcagctc cagtggctga accgccgggc        100
caatgccctc ctggccaatg gcgtggagct gagagataac cagctggtgg        150
tgccatcaga gggcctgtac ctcatctact cccaggtcct cttcaagggc        200
caaggctgcc cctccaccca tgtgctcctc acccacacca tcagccgcat        250
cgccgtctcc taccagacca aggtcaacct cctctctgcc atcaagagcc        300
cctgccagag ggagacccca gagggggctg aggccaagcc ctggtatgag        350
cccatctatc tgggaggggt cttccagctg agaagggtg accgactcag         400
cgctgagatc aatcggcccg actatctcga ctttgccgag tctgggcagg        450
tctactttgg gatcattgcc ctgtgatcta ga                           482
```

<210> SEQ ID NO 55
<211> LENGTH: 157
<212> TYPE: PRT
<213> ORGANISM: Homo sapiens
<220> FEATURE:
<223> OTHER INFORMATION: amino acid sequence of a TNF fragment

<400> SEQUENCE: 55

```
Met Val Ser Ser Ser Arg Thr Pro Ser Asp Lys Pro Val Ala His Val
              5                  10                  15
Val Ala Asn Pro Gln Ala Glu Gly Gln Leu Gln Trp Leu Asn Arg Arg
         20                  25                  30
Ala Asn Ala Leu Leu Ala Asn Gly Val Glu Leu Arg Asp Asn Gln Leu
     35                  40                  45
Val Val Pro Ser Glu Gly Leu Tyr Leu Ile Tyr Ser Gln Val Leu Phe
 50                  55                  60
Lys Gly Gln Gly Cys Pro Ser Thr His Val Leu Leu Thr His Thr Ile
65                  70                  75                  80
Ser Arg Ile Ala Val Ser Tyr Gln Thr Lys Val Asn Leu Leu Ser Ala
                 85                  90                  95
Ile Lys Ser Pro Cys Gln Arg Glu Thr Pro Glu Gly Ala Glu Ala Lys
            100                 105                 110
Pro Trp Tyr Glu Pro Ile Tyr Leu Gly Gly Val Phe Gln Leu Glu Lys
        115                 120                 125
Gly Asp Arg Leu Ser Ala Glu Ile Asn Arg Pro Asp Tyr Leu Asp Phe
    130                 135                 140
Ala Glu Ser Gly Gln Val Tyr Phe Gly Ile Ile Ala Leu
145                 150                 155
```

<210> SEQ ID NO 56
<211> LENGTH: 6047
<212> TYPE: DNA
<213> ORGANISM: Artificial Sequence
<220> FEATURE:
<223> OTHER INFORMATION: Heavy chain expression vector pREN-DHFR-TNF
      which is a mammalian cell expression vector used to produce
      chimeric and reshaped human antibodies with parts of the human
      gamma-1 heavy chain fol

<400> SEQUENCE: 56

```
ctcgagagcg gcagtgagc gcaacgcaat taatgtgagt tagctcactc            50
attaggcacc ccaggcttta cactttatgc tccggctcg tatgttgtgt           100
ggagattgtg agcggataac aatttcacac agaattcgtg aggctccggt          150
```

-continued

```
gcccgtcagt gggcagagcg cacatcgccc acagtccccg agaagttggg        200
gggaggggtc ggcaattgaa ccggtgccta gagaaggtgg cgcggggtaa        250
actgggaaag tgatgtcgtg tactggctcc gccttttttcc cgagggtggg       300 ggagaaccgt atataagtgc agtagtcgcc gtgaacgttc tttttcgcaa        350
cgggtttgcc gccagaacac aggtaagtgc cgtgtgtggt tcccgcgggc        400
ctggcctctt tacgggttat ggcccttgcg tgccttgaat tacttccacg        450
cccctggctg cagtacgtga ttcttgatcc cgagcttcgg gttggaagtg        500
ggtgggagag ttcgaggcct tgcgcttaag gagccccttc gcctcgtgct        550
tgagttgagg cctggcctgg gcgctggggc cgccgcgtgc gaatctggtg        600
gcaccttcgc gcctgtctcg ctgctttcga taagtctcta gccatttaaa       650
atttttgatg acctgctgcg acgcttttttt tctggcaaga tagtcttgta      700
aatgcgggcc aagatctgca cactggtatt tcggtttttg gggccgcggg        750
cggcgacggg gcccgtgcgt cccagcgcac atgttcggcg aggcggggcc        800
tgcgagcgcg gccaccgaga atcggacggg ggtagtctca agctggccgg        850
cctgctctgg tgcctggcct cgcgccgccg tgtatcgccc cgccctgggc        900
ggcaaggctg gcccggtcgg caccagttgc gtgagcggaa agatggccgc        950
ttcccggccc tgctgcaggg agctcaaaat ggaggacgcg gcgctcggga       1000
gagcgggcgg gtgagtcacc cacacaaagg aaaagggcct ttccgtcctc       1050
agccgtcgct tcatgtgact ccacggagta ccgggcgccg tccaggcacc       1100
tcgattagtt ctcgagcttt tggagtacgt cgtctttagg ttggggggag       1150
gggttttatg cgatggagtt tccccacact gagtgggtgg agactgaagt       1200
taggccagct tggcacttga tgtaattctc cttggaattt gcccttttg        1250 agtttggatc ttggttcatt ctcaagcctc agacagtggt tcaaagtttt      1300
tttcttccat ttcaggtgta cgcgtctcgg gaagctttag tttaaacgcc      1350
ggatcctctg cgcctgggcc cagctctgtc ccacaccgcg gtcacatggc      1400
```

| accacctctc ttgcagcc tcc acc aag ggc cca tcg gtc ttc ccc ctg<br>                  Ser Thr Lys Gly Pro Ser Val Phe Pro Leu<br>                           5                 10 | 1448 |
|---|---|
| gca ccc tcc tcc aag agc acc tct ggg ggc aca gcg gcc ctg ggc<br>Ala Pro Ser Ser Lys Ser Thr Ser Gly Gly Thr Ala Ala Leu Gly<br>                15                 20               25 | 1493 |
| tgc ctg gtc aag gac tac ttc ccc gaa ccg gtg acg gtg tcg tgg<br>Cys Leu Val Lys Asp Tyr Phe Pro Glu Pro Val Thr Val Ser Trp<br>                30                 35               40 | 1538 |
| aac tca ggc gcc ctg acc agc ggc gtg cac acc ttc ccg gct gtc<br>Asn Ser Gly Ala Leu Thr Ser Gly Val His Thr Phe Pro Ala Val<br>                45                 50               55 | 1583 |
| cta cag tcc tca gga ctc tac tcc ctc agc agc gtg gtg acc gtg<br>Leu Gln Ser Ser Gly Leu Tyr Ser Leu Ser Ser Val Val Thr Val<br>                60                 65               70 | 1628 |
| ccc tcc agc agc ttg ggc acc cag acc tac atc tgc aac gtg aat<br>Pro Ser Ser Ser Leu Gly Thr Gln Thr Tyr Ile Cys Asn Val Asn<br>                75                 80               85 | 1673 |
| cac aag ccc agc aac acc aag gtg gac aag aaa gtt gag ccc aaa<br>His Lys Pro Ser Asn Thr Lys Val Asp Lys Lys Val Glu Pro Lys<br>                90                 95            100 | 1718 |

-continued

| | |
|---|---|
| tct tgt gac aaa act cac aca tgc cca ccg tgc cca ggt gga ggt<br>Ser Cys Asp Lys Thr His Thr Cys Pro Pro Cys Pro Gly Gly Gly<br>              105                          110                          115 | 1763 |
| gga tca cca atg gtc tca tct tct cga acc ccg agt gac aag cct<br>Gly Ser Pro Met Val Ser Ser Ser Arg Thr Pro Ser Asp Lys Pro<br>              120                          125                          130 | 1808 |
| gta gcc cat gtt gta gca aac cct caa gct gag ggg cag ctc cag<br>Val Ala His Val Val Ala Asn Pro Gln Ala Glu Gly Gln Leu Gln<br>              135                          140                          145 | 1853 |
| tgg ctg aac cgc cgg gcc aat gcc ctc ctg gcc aat ggc gtg gag<br>Trp Leu Asn Arg Arg Ala Asn Ala Leu Leu Ala Asn Gly Val Glu<br>              150                          155                          160 | 1898 |
| ctg aga gat aac cag ctg gtg gtg cca tca gag ggc ctg tac ctc<br>Leu Arg Asp Asn Gln Leu Val Val Pro Ser Glu Gly Leu Tyr Leu<br>              165                          170                          175 | 1943 |
| atc tac tcc cag gtc ctc ttc aag ggc caa ggc tgc ccc tcc acc<br>Ile Tyr Ser Gln Val Leu Phe Lys Gly Gln Gly Cys Pro Ser Thr<br>              180                          185                          190 | 1988 |
| cat gtg ctc ctc acc cac acc atc agc cgc atc gcc gtc tcc tac<br>His Val Leu Leu Thr His Thr Ile Ser Arg Ile Ala Val Ser Tyr<br>              195                          200                          205 | 2033 |
| cag acc aag gtc aac ctc ctc tct gcc atc aag agc ccc tgc cag<br>Gln Thr Lys Val Asn Leu Leu Ser Ala Ile Lys Ser Pro Cys Gln<br>              210                          215                          220 | 2078 |
| agg gag acc cca gag ggg gct gag gcc aag ccc tgg tat gag ccc<br>Arg Glu Thr Pro Glu Gly Ala Glu Ala Lys Pro Trp Tyr Glu Pro<br>              225                          230                          235 | 2123 |
| atc tat ctg gga ggg gtc ttc cag ctg gag aag ggt gac cga ctc<br>Ile Tyr Leu Gly Gly Val Phe Gln Leu Glu Lys Gly Asp Arg Leu<br>              240                          245                          250 | 2168 |
| agc gct gag atc aat cgg ccc gac tat ctc gac ttt gcc gag tct<br>Ser Ala Glu Ile Asn Arg Pro Asp Tyr Leu Asp Phe Ala Glu Ser<br>              255                          260                          265 | 2213 |
| ggg cag gtc tac ttt ggg atc att gcc ctg tga tctagaaact<br>Gly Gln Val Tyr Phe Gly Ile Ile Ala Leu<br>              270                          275 | 2256 |
| aactaagcta gcaacggttt ccctctagcg ggatcaattc cgcccccccc | 2306 |
| ccctaacgtt actggccgaa gccgcttgga ataaggccgg tgtgcgtttg | 2356 |
| tctatatgtt attttccacc atattgccgt cttttggcaa tgtgagggcc | 2406 |
| cggaaacctg gccctgtctt cttgacgagc attcctaggg gtctttcccc | 2456 |
| tctcgccaaa ggaatgcaag gtctgttgaa tgtcgtgaag gaagcagttc | 2506 |
| ctctggaagc ttcttgaaga caaacaacgt ctgtagcgac cctttgcagg | 2556 |
| cagcggaacc cccacctggc gacaggtgc ctctgcggcc aaaagccacg | 2606 |
| tgtataagat acacctgcaa aggcggcaca ccccagtgcc acgttgtga | 2656 |
| gttggatagt tgtggaaaga gtcaaatggc tctcctcaag cgtattcaac | 2706 |
| aaggggctga aggatgccca gaaggtaccc cattgtatgg gatctgatct | 2756 |
| ggggcctcgg tgcacatgct ttacgtgtgt ttagtcgagg ttaaaaaacg | 2806 |
| tctaggcccc ccgaaccacg gggacgtggt tttcctttga aaaacacgat | 2856 |
| aataccatgg ttcgaccatt gaactgcatc gtcgccgtgt cccaaaatat | 2906 |
| ggggattggc aagaacggag acctaccctg gcctccgctc aggaacgagt | 2956 |
| tcaagtactt ccaaagaatg accacaacct cttcagtgga aggtaaacag | 3006 |
| aatctggtga ttatgggtag gaaaacctgg ttctccattc ctgagaagaa | 3056 |

```
tcgaccttta aaggacagaa ttaatggttc gatatagttc tcagtagaga          3106
actcaaagaa ccaccacgag gagctcattt tcttgccaaa agtttggatg          3156
atgccttaag acttattgaa caaccggaat tggcaagtaa agtagacatg          3206
gtttggatag tcggaggcag ttctgtttac caggaagcca tgaatcaacc          3256
aggccacctc agactctttg tgacaaggat catgcaggaa tttgaaagtg          3306
acacgttttt cccagaaatt gatttgggga aatataaact tctcccagaa          3356
tacccaggcg tcctctctga ggtccaggag gaaaaaggca tcaagtataa          3406
gtttgaagtc tacgagaaga aagactaaca ggaagatgct ttcaagttct          3456
ctgctcccct cctaaagcta tgcattttta taagaccatg ggactttgc           3506
tggtcgatcg acctggcgta atagcgaaga ggcccgcacc gatcgccctt          3556
cccaacagtt gcgcagcctg aatggcgaat gggacgcgcc ctgtagcggc          3606
gcattaagcg cggcgggtgt ggtggttacg cgcagcgtga ccgctacact          3656
tgccagcgcc ctagcgcccg ctcctttcgc tttcttccct tcctttctcg          3706
ccacgttcgc cggctttccc cgtcaagctc taaatcgggg gctcccttta          3756
gggttccgat ttagtgcttt acggcacctc gaccccaaaa aacttgatta          3806
gggtgatggt tcacgtagtg ggccatcgcc ctgatagacg gtttttcgcc          3856
tttgacgttg gagtccacgt tctttaatag tggactcttg ttccaaactg          3906
gaacaacact caaccctatc tcggtctatt tataagggat tttgccgatt          3956
tcggcctatt ggttaaaaaa tgagctgatt taacaaaatt taacgcgaat          4006
tttaacaaaa tattaacgct tacaatttag gtggcacttt tcggggaaat          4056
gtgcgcggaa cccctatatt tgtttatttt tctaaataca ttcaaatatg          4106
tatccgctca tgagacaata accctgataa atgcttcaat aatattgaaa          4156
aaggaagagt atgagtattc aacatttccg tgtcgccctt attccctttt          4206
ttgcggcatt ttgccttact gtttttgctc acccagaaac gctggtgaaa          4256
gtaaaagatg ctgaagatca gttgggtgca cgagtgggtt acatcgaact          4306
ggatctcaac agcggtaaga tccttgagag ttttcgcccc gaagaacgtt          4356
ttccaatgat gagcactttt aaagttctgc tatgtggcgc ggtattatcc          4406
cgtattgacg ccgggcaaga gcaactcggt cgccgcatac actattctca          4456
gaatgacttg gttgagtact caccagtcac agaaaagcat attacggatg          4506
gcatgacagt aagagaatta tgcagtgctg ccataaccat gagtgataac          4556
actgcggcca acttacttct gacaacgatc ggaggaccga aggagctaac          4606
cgcttttttg cacaacatgg ggatcatgt aactcgcctt gatcgttggg           4656
aaccggagct gaatgaagcc ataccaaacg acgagcgtga ccaccacgatg         4706
cctgtagcaa tggcaacaac gttgcgcaaa ctattaactg gcgaactact          4756
tactctagct tcccggcaac aattaataga ctggatggag gcggataaag          4806
ttgcaggacc acttctgcgc tcggcccttc cggctggctg gtttattgct          4856
gataaatctg gagccggtga gcgtgggtct cgcggtatca ttgcagcact          4906
ggggccagat ggtaagccct cccgtatcgt agttatctac acgacgggga          4956
gtcaggcaac tatggatgaa cgaaatagac agatcgctga gataggtgcc          5006
```

-continued

```
tcactgatta agcattggta actgtcagac caagtttact catatatact         5056
ttagattgat ttaaaacttc atttttaatt taaaaggatc taggtgaaga         5106 tccttttga taatctcatg accaaaatcc cttaacgtga gttttcgttc          5156
cactgagcgt cagaccccgt agaaaagatc aaaggatgtt cttgagatcc         5206 ttttttctg cacgtaatct gctgcttgca aacaaaaaac caccgctacc          5256
agcggtggtt tgtttgccgg atcaagagct accaactctt tttccgaagg         5306
taactggctt cagcagagcg cagataccaa atactgtcct tctagtgtag         5356
ccgtagttag gccaccactt caagaactct gtagcaccgc ctacatacct         5406
cgctctgcta atcctgttac cagtggctgc tgccagtggc gataagtcgt         5456
gtcttaccgg gttggactca agacgatagt taccggataa ggcgcagcgg         5506
tcgggctgaa cggggggttc gtgcacacag cccagcttgg agcgaacgac         5556
ctacaccgaa ctgagatacc tacagcgtga gctatgagaa agcgccacgc         5606
ttcccgaagg gagaaaggcg gacaggtatc cggtaagcgg cagggtcgga         5656
acaggagagc gcacgaggga gcttccaggg ggaaacgcct ggtatcttta         5706
tagtcctgtc gggtttcgcc acctctgact tgagcgtcga ttttgtgat          5756 gctcgtcagg ggggcggagc ctatggaaaa acgccagcaa cgcggccttt         5806
ttacggttcc tggccttttg ctggccttt gctcacatgt tctttcctgc          5856
gttatcccct gattctgtgg ataaccgtat taccgccttt gagtgagctg         5906
ataccgctcg ccgcagccga acgaccgagc gcagcgagtc agtgagcgag         5956
gaagcggaag agcgcccaat acgcaaaccg cctctccccg cgcgttggcc         6006
gattcattaa tgcaggtatc acgaggccct ttcgtcttca c                  6047
```